(12) United States Patent
Altermann et al.

(10) Patent No.: US 12,420,027 B2
(45) Date of Patent: Sep. 23, 2025

(54) DEVICE FOR ADMINISTERING A FLUID

(71) Applicant: Henke-Sass, Wolf GmbH, Tuttlingen (DE)

(72) Inventors: Frank Altermann, Tuttlingen (DE); Robin Sauter, Tuttlingen (DE); Maikel Wiedmann, Immendingen (DE); Daniel Seeh, Immendingen (DE); Anika Schmidt, Fridingen (DE)

(73) Assignee: Henke-Sass, Wolf GmbH, Tuttlingen (DE)

( * ) Notice: Subject to any disclaimer, the term of this patent is extended or adjusted under 35 U.S.C. 154(b) by 875 days.

(21) Appl. No.: 17/640,051

(22) PCT Filed: Jul. 9, 2020

(86) PCT No.: PCT/EP2020/069450
§ 371 (c)(1),
(2) Date: Mar. 3, 2022

(87) PCT Pub. No.: WO2021/043471
PCT Pub. Date: Mar. 11, 2021

(65) Prior Publication Data
US 2022/0313922 A1     Oct. 6, 2022

(30) Foreign Application Priority Data

Sep. 4, 2019     (DE) .................. 102019123731.9

(51) Int. Cl.
*A61M 5/315*     (2006.01)
*A61M 5/30*     (2006.01)
*A61M 5/31*     (2006.01)

(52) U.S. Cl.
CPC .......... *A61M 5/31576* (2013.01); *A61M 5/30* (2013.01); *A61M 5/3153* (2013.01);
(Continued)

(58) Field of Classification Search
CPC ............ A61M 5/30; A61M 2005/3115; A61M 2005/202; A61M 5/204; A61M 2205/3327; A61D 7/00
See application file for complete search history.

(56) References Cited

U.S. PATENT DOCUMENTS 2,717,597 A     9/1955  Hein, Jr.
2,928,390 A     3/1960  Venditty et al.
(Continued)

FOREIGN PATENT DOCUMENTS

CN     2789458 Y     6/2006
CN     103550848 A     2/2014
(Continued)

OTHER PUBLICATIONS

International Preliminary Report on Patentability rendered by the International Bureau of WIPO for PCT/EP2020/069450, dated Mar. 8, 2022, 9 pages.
(Continued)

*Primary Examiner* — Michael J Tsai
*Assistant Examiner* — Benjamin Koo
(74) *Attorney, Agent, or Firm* — Skaar Ulbrich Macari, P.A.

(57) ABSTRACT

A device for administering a fluid can include a cylinder, a piston displaceable in the cylinder and connected to a piston rod, and a tensioning device connected to the piston rod. The tensioning device includes a ramp rotatable via a motor, and a ramp track extending along a helical line. The tensioning device includes a roller which is in contact with the ramp track. To perform a tensioning procedure, the ramp track is rotated such that the roller runs on the region of inclination as far as the second plateau so the piston is moved to its rear end position. To perform a dispensing procedure, the ramp track is rotated until the roller runs over a transfer region and
(Continued)

is accelerated toward the first plateau, thereby the piston is moved toward an open dispensing end. A control unit determines whether the tensioning procedure and/or dispensing procedure has taken place correctly.

14 Claims, 21 Drawing Sheets

(52) U.S. Cl.
CPC . *A61M 5/31548* (2013.01); *A61M 2005/3115* (2013.01); *A61M 2205/3365* (2013.01); *A61M 2205/3375* (2013.01)

(56) References Cited

U.S. PATENT DOCUMENTS

| | | | |
|---|---|---|---|
| 3,057,349 | A | 10/1962 | Ismach |
| 3,973,697 | A | 8/1976 | Crum et al. |
| 4,402,252 | A | 9/1983 | Klumpp |
| 4,416,279 | A | 11/1983 | Lindner et al. |
| 5,480,381 | A * | 1/1996 | Weston ............ G01N 33/54313 604/68 |
| 6,796,970 | B1 | 9/2004 | Klitmose et al. |
| 9,402,961 | B2 | 8/2016 | Leak et al. |
| 12,064,604 | B2 * | 8/2024 | Altermann ............ A61M 5/204 |
| 2004/0019333 | A1 | 1/2004 | Graf et al. |
| 2004/0186431 | A1 | 9/2004 | Graf et al. |
| 2005/0267403 | A1 | 12/2005 | Landau et al. |
| 2006/0173439 | A1 | 8/2006 | Thorne, Jr. et al. |
| 2006/0217661 | A1 | 9/2006 | Meijering et al. |
| 2006/0247500 | A1 | 11/2006 | Voegele et al. |
| 2007/0191770 | A1 | 8/2007 | Moberg et al. |
| 2008/0195051 | A1 | 8/2008 | Graf et al. |
| 2010/0004621 | A1 | 1/2010 | Toles et al. |
| 2011/0224613 | A1 | 9/2011 | D'Antonio et al. |
| 2013/0096495 | A1 | 4/2013 | Holmqvist et al. |
| 2013/0190117 | A1 | 7/2013 | Bauer et al. |
| 2014/0207080 | A1 | 7/2014 | Allerdings |
| 2014/0312074 | A1 | 10/2014 | Madsen et al. |
| 2015/0025500 | A1 | 1/2015 | Piehl et al. |
| 2015/0065958 | A1 | 3/2015 | Teutsch et al. |
| 2015/0202368 | A1 | 7/2015 | Carrel et al. |
| 2015/0265776 | A1 | 9/2015 | Beek et al. |
| 2016/0206826 | A1 | 7/2016 | Bilton et al. |
| 2016/0296710 | A1 | 10/2016 | Bainton et al. |
| 2017/0266394 | A1 | 9/2017 | Admati et al. |
| 2017/0354782 | A1 | 12/2017 | Quinn et al. |
| 2018/0154084 | A1 | 6/2018 | Fabien et al. |
| 2019/0000489 | A1 | 1/2019 | McCoy et al. |
| 2019/0022306 | A1 | 1/2019 | Gibson et al. |
| 2019/0091399 | A1 | 3/2019 | Calasso et al. |
| 2020/0023128 | A1 | 1/2020 | Fachinger et al. |
| 2021/0023303 | A1 | 1/2021 | Altermann et al. |
| 2021/0052815 | A1 | 2/2021 | Altermann et al. |
| 2021/0069417 | A1 | 3/2021 | Altermann et al. |
| 2021/0077729 | A1 | 3/2021 | Altermann et al. |
| 2021/0196895 | A1 | 7/2021 | Lehmann et al. |

FOREIGN PATENT DOCUMENTS

| | | |
|---|---|---|
| CN | 106512149 A | 3/2017 |
| DE | 102017108088 A1 | 10/2018 |
| GB | 798826 A | 7/1958 |
| GB | 843520 A | 8/1960 |
| GB | 993309 A | 5/1965 |
| WO | 2010106031 A1 | 9/2010 |
| WO | 2018107220 A1 | 6/2018 |

OTHER PUBLICATIONS

International Search Report rendered by the International Bureau of WIPO for PCT/EP2020/069450, dated Oct. 1, 2020, 4 pages.

* cited by examiner

DEVICE FOR ADMINISTERING A FLUID

PRIORITY

This application claims the priority of German patent application DE 10 2019 123 731.9 filed Sep. 4, 2019, which is hereby incorporated herein by reference in its entirety.

FIELD

The present invention relates to a device for administering a fluid, which device can be designed, for example, as a needle-free self-filling syringe with which a liquid medicament, a liquid pharmaceutical product, a liquid vaccine or the like can be administered to animals by intramuscular administration.

BACKGROUND

Such a device for administering a fluid should be as light as possible, and thus able to be carried with one hand for a long period of time by a user, and at the same time should permit the desired needle-free intramuscular injection.

SUMMARY

It is an object of certain embodiments of the invention to provide a device for administering a fluid.

The device according to certain example embodiments for administering a fluid comprises a cylinder, which has an open dispensing end, a piston, which is displaceable in the cylinder between a front end position and rear end position and is connected to a piston rod which, along a first direction, protrudes from a rear end of the cylinder opposite the open dispensing end, a nonreturn valve (which acts as an outlet valve) closing the open dispensing end, and a tensioning device connected to the piston rod. The tensioning device can move the piston rod along the first direction in a tensioning procedure until the piston is in its rear end position, in order to thereby fill the cylinder with the fluid to be administered and to pretension the piston rod toward the open dispensing end. For this purpose, the device can have an attachment which leads into the cylinder. A hose or a container with the fluid to be administered, for example, can be fastenable to the attachment and can be fastened for use of the device. The attachment can preferably have a nonreturn valve which is designed as an inlet valve and opens during the tensioning procedure and closes during the administering of the fluid. Accordingly, the outlet valve closes during the tensioning procedure and opens during the administering of the fluid.

Moreover, the tensioning device, when the piston is in its rear end position, can release the piston rod in a dispensing procedure such that, owing to the pretension which is present, the piston is moved counter to the first direction toward the open dispensing end and, in the process, fluid in the cylinder is dispensed via the nonreturn valve for administration.

The tensioning device can have a ramp which is rotatable by means of a motor and which has a ramp track extending along a helical line, wherein the ramp track ascends from a first plateau along a region of inclination to a second plateau and descends from the second plateau to the first plateau via a transition flank, wherein the ramp track has a transfer region connecting the second plateau and the transition flank. The tensioning device can moreover have a roller which is in contact with the ramp track and which is mounted rotatably in a driver, the latter being connected to the piston rod, and therefore, upon rotation of the ramp along a first rotation direction, the ramp track runs below the thus rotating roller. For the tensioning procedure, the ramp track can be rotated along the first rotation direction such that the roller runs on the region of inclination as far as the second plateau and the piston is thereby moved to its rear end position. For the dispensing procedure, starting from a contact of the roller with the second plateau, the tensioning device can rotate the ramp track along the first rotation direction until the roller runs over the transfer region and, on account of the pretensioning, accelerates toward the first plateau, as a result of which the piston is moved toward the open dispensing end.

The device is preferably designed as a self-filling syringe for needle-free administration (in particular intramuscular administration) to animals and/or humans.

The motor can be connected to the ramp via a coupling, wherein, for the rotation of the ramp, the coupling transmits the torque, which is provided by the motor, in the first rotation direction and, in the process, provides a freewheel counter to the first rotation direction, the freewheel being configured in such a manner that it covers at least an rotation angle range which corresponds to the transfer region.

The coupling can be designed in such a manner that the freewheel covers a rotation angle range which corresponds to no more than twice the transfer region. The freewheel can cover in particular the rotation angle range which is larger by 10%, 20%, 30%, 40%, 50%, 60%, 70%, 80% or 90% than the transfer region.

The coupling can have a first coupling part, which is connected to the motor, and a second coupling part, which is connected to the ramp. One of the two coupling parts can have a protruding engagement element and the other of the two coupling parts a recess into which the engagement element protrudes. The extent of the engagement element in the first rotation direction can be smaller by at least the rotation angle range covering the transfer region than the extent of the recess in the first rotation direction. The extent of the recess in the first rotation direction is therefore greater than the extent of the engagement element in the first rotation direction, as a result of which the desired freewheel is provided.

A spring can be arranged between a side surface of the engagement element and a side surface of the recess, said side surfaces facing each other in the first rotation direction. In particular, a spring can be arranged between all opposite side surfaces of engagement element and recess. The spring/springs can be fastened to the engagement element.

The spring/springs can be designed as compression springs. In particular, they can be realized as disk springs.

The engagement element can be designed as a web.

The first coupling part can have the engagement element. Furthermore, the ramp can comprise a base as the second coupling part, with the recess being formed in the base.

One of the two coupling parts can have a plurality of protruding engagement elements which are spaced apart from one another in the first direction. The other of the two coupling parts can have a plurality of recesses into which the engagement elements protrude. The extent of each engagement element in the first rotation direction is smaller at least by the rotation angle range covering the transfer region than the extent of the corresponding recess in the first rotation direction.

The ramp track can run on the face side of a wall extending along a circular path, wherein a cover is provided which engages over the ramp track, the driver and the roller and which has at least one scraper which extends counter to the first direction and extends within the wall as far as the inner side of the wall and thus scrapes off lubricant located in the inner side from the inner side.

The cover can have a plurality of scrapers which extend counter to the first direction and which each extend within the wall in the direction of the inner side of the wall and thus scrape off lubricant located in the inner side from the inner side, the scrapers being spaced apart from one another along the first direction.

The scrapers can differ in their length counter to the first direction.

Furthermore, the scrapers can differ in their extent in the direction toward the inner side.

The scraper or the scrapers can be formed on a frustoconical central part. In particular, they can extend radially from the frustoconical central part. The frustoconical central part can extend counter to the first direction. In particular, the frustoconical central part can extend as far as the base of the ramp.

The central part can also have any other form. In particular, it can be cylindrical.

The piston rod can be connected to the driver via a joint.

In particular, in order to form the joint, that end of the piston rod which faces away from the piston can be rounded and mounted movably in a bed.

The bed can be formed on a connecting part which, by means of a screw screwed into the rounded end, presses against the rounded end of the piston rod. The bed can be formed by a curved side of a washer (or of a leveling washer).

Furthermore, the joint can have two washers (or leveling washers) arranged one on the other and the mutually facing sides of which are curved such that they move against each other during rotation of the piston rod. The two washers can be arranged on a side of the connecting part that faces away from the rounded end of the piston rod.

The joint can be designed as a rotary joint and/or as a joint with precisely one degree of freedom.

The joint can permit a translational movement (preferably precisely one translational movement) transversely with respect to the longitudinal direction of the piston rod.

The administering device can have precisely one cylinder with precisely one piston and precisely one piston rod, wherein the tensioning device has two helical screws which run parallel to each other and which both, when the piston is in its rear end position, contribute to the pretensioning which is present.

The two helical springs can be arranged spaced apart from each other transversely with respect to their longitudinal direction and/or can have the same dimensions.

In particular, the helical springs can be arranged in such a manner that their longitudinal directions are parallel to the longitudinal direction of the piston rod.

The helical springs can be designed as compression springs.

The piston rod can be connected to two guide rods via a connecting part, wherein each guide rod extends within one of the helical springs.

The tensioning device can have at least three helical springs running parallel to one another. In particular, the helical springs can be arranged symmetrically with respect to the motor in a plane perpendicular to the longitudinal direction of the helical springs.

The device for administering a fluid can comprise a front part, which has the cylinder and the open dispensing end, and a rear part, which has the tensioning device, wherein the front part and the rear part are formed from different materials.

The material of the front part can comprise titanium, steel or plastic and the material of the rear part can comprise titanium, aluminum, magnesium or plastic.

The device can have a housing surrounding the front part and the rear part, wherein a portion of the front part protrudes from the housing.

The device can comprise a dose setting means with a spacer and a movement unit, wherein the movement unit can move the spacer, when the piston is in its rear end position, from a neutral position, in which the spacer is not positioned between the driver and the cylinder, into an active position between the driver and the cylinder such that the driver, after the roller has run over the transfer region, is stopped by the spacer and therefore the piston stroke during the movement of the piston to the open dispensing end is shorter in comparison to the case in which the spacer is in its neutral position.

The spacer can have a threaded bore into which a threaded rod protrudes, said threaded rod being rotated in order to move the spacer between its neutral position and its active position.

The spacer can be guided in such a manner that the spacer is movable only in a plane perpendicular to the piston rod.

The spacer can be designed in such a manner that, when the driver is stopped by the spacer, the roller is not in contact with the spacer.

The spacer can have a first abutment region and a second abutment region for the driver, wherein the extent of the spacer along the first direction is smaller for the first abutment region than for the second abutment region, and therefore different shortenings of the piston stroke can be set, depending on whether the first or second abutment region is moved into the active position of the spacer.

Of course, the spacer can also have three or more abutment regions, wherein the extent of the spacer along the first direction differs for the abutment regions, and therefore different shortenings of the piston stroke can be set, depending on which abutment region is moved into the active position of the spacer.

The device can have a control unit which carries out a measurement of a characteristic variable during a tensioning procedure and/or dispensing procedure and determines therefrom, by comparing with at least one specified value, whether the tensioning procedure and/or dispensing procedure has taken place correctly. In particular, the measurement of the characteristic variable can be carried out during the dispensing procedure and the preceding tensioning procedure and from this, by comparing with the at least one specified value, it is determined whether both the tensioning procedure and the dispensing procedure have taken place correctly.

The current consumption of the motor, the acceleration acting on the administering device, and/or the sound (or the noises; e.g. frequency spectrum, frequency (frequencies), pitch, energy and/or volume) can be measured as a characteristic variable.

A temporal desired profile of the current consumption with a lower limit and an upper limit can be predefined as the at least one specified value, wherein the control unit determines the tensioning procedure as being correct when the current consumption measured throughout the entire tensioning procedure is not smaller than the lower limit and not greater than the upper limit.

A temporal desired profile of the acceleration with an upper limit can be predefined as the at least one specified value, wherein the control unit determines the dispensing procedure as being correct when the acceleration measured throughout the entire dispensing procedure is not greater than the upper limit.

A first upper desired frequency and a first lower desired frequency and/or a first upper and a first lower desired amplitude can be predefined as the at least one specified value, wherein the control unit determines the dispensing procedure as being correct when a main frequency of the measured frequency spectrum lies between the first upper desired frequency and the first lower desired frequency and/or the amplitude of the main frequency of the measured frequency spectrum lies between the first upper desired amplitude and the first lower desired amplitude.

The main frequency is understood here as meaning in particular the frequency of the measured frequency spectrum that has the greatest amplitude. The main frequency is customarily the frequency which determines the pitch.

The first upper desired frequency can be greater by 0.5%, 1%, 1.5%, 2%, 2.5%, 3%, 3.5%, 4%, 4.5%, 5%, 6%, 7%, 8%, 9%, 10%, 12%, 14% or 15% than a predetermined first desired main frequency. Furthermore, the first lower desired frequency can be smaller by 0.5%, 1%, 1.5%, 2%, 2.5%, 3%, 3.5%, 4%, 4.5%, 5%, 6%, 7%, 8%, 9%, 10%, 12%, 14% or 15% than the predetermined first desired main frequency.

The first upper desired amplitude can be greater by 0.5%, 1%, 1.5%, 2%, 2.5%, 3%, 3.5%, 4%, 4.5%, 5%, 6%, 7%, 8%, 9%, 10%, 12%, 14% or 15% than a predetermined first desired main amplitude. Furthermore, the first lower desired amplitude can be smaller by 0.5%, 1%, 1.5%, 2%, 2.5%, 3%, 3.5%, 4%, 4.5%, 5%, 6%, 7%, 8%, 9%, 10%, 12%, 14% or 15% than the predetermined first desired main amplitude.

Furthermore, a second upper desired frequency and a second lower desired frequency and/or a second upper desired amplitude and a second lower desired amplitude can be predefined as the at least one specified value, wherein the control unit determines the dispensing procedure as being correct when a first secondary frequency of the measured frequency spectrum lies between the second upper desired frequency and the second lower desired frequency and/or the amplitude of the first secondary frequency of the measured frequency spectrum lies between the second upper desired amplitude and the second lower desired amplitude.

The first secondary frequency is understood here as meaning in particular the frequency of the measured frequency spectrum that has the second highest amplitude and therefore the greatest amplitude after the main frequency.

The second upper desired frequency can be greater by 0.5%, 1%, 1.5%, 2%, 2.5%, 3%, 3.5%, 4%, 4.5%, 5%, 6%, 7%, 8%, 9%, 10%, 12%, 14% or 15% than a predefined first desired secondary frequency. Furthermore, the second lower desired frequency can be smaller by 0.5%, 1%, 1.5%, 2%, 2.5%, 3%, 3.5%, 4%, 4.5%, 5%, 6%, 7%, 8%, 9%, 10%, 12%, 14% or 15% than the predefined first desired secondary frequency.

The second upper desired amplitude can be greater by 0.5%, 1%, 1.5%, 2%, 2.5%, 3%, 3.5%, 4%, 4.5%, 5%, 6%, 7%, 8%, 9%, 10%, 12%, 14% or 15% than a predefined first desired secondary amplitude. Furthermore, the second lower desired amplitude can be smaller by 0.5%, 1%, 1.5%, 2%, 2.5%, 3%, 3.5%, 4%, 4.5%, 5%, 6%, 7%, 8%, 9%, 10%, 12%, 14% or 15% than the predefined first desired secondary amplitude.

Of course, a second, third, fourth, fifth secondary frequency and/or further secondary frequencies (the amplitudes of which are in each case smaller) can be measured in the same way and taken into consideration for evaluating the dispensing procedure.

The dispensing procedure is determined as being correct when the main frequency of the measured frequency spectrum is smaller than the desired frequency, and/or the amplitude of the main frequency of the measured frequency spectrum is greater than the desired amplitude. The main frequency is understood here as meaning in particular the frequency of the measured frequency spectrum that has the greatest amplitude. The main frequency is customarily the frequency which determines the pitch.

The duration of the tensioning procedure can be measured as a characteristic variable.

A first desired duration can be predefined as a specified value, wherein the control unit determines the tensioning procedure as being correct when the measured duration is greater than the first desired duration.

A second desired duration can be predefined as a specified value, wherein the control unit determines the tensioning procedure as being correct when the measured duration is smaller than the second desired duration.

Furthermore, the rotation angle covered by the ramp track along the first rotation direction during the tensioning procedure can be measured as a characteristic variable.

A desired rotation angle can be predefined as a specified value, wherein the control unit determines the tensioning procedure as being correct when the measured rotation angle which is covered is greater than the desired rotation angle.

It will be appreciated that the features mentioned above and the features still to be explained below can be used not only in the specified combinations but also in other combinations or on their own, without departing from the scope of the present invention.

The invention is explained in even more detail below on the basis of exemplary embodiments, with reference being made to the appended drawings, which likewise disclose features essential to the invention. These exemplary embodiments are only illustrative and should not be construed as restrictive. For example, a description of an exemplary embodiment with a multiplicity of elements or components should not be construed as meaning that all of these elements or components are necessary for implementation. Rather, other exemplary embodiments can also contain alternative elements and components, fewer elements or components, or additional elements or components. Elements or components of different exemplary embodiments can be combined with one another, unless stated otherwise. Modifications and variations that are described for one of the exemplary embodiments can also be applicable to other exemplary embodiments. In order to avoid repetition, the same elements or corresponding elements in different figures are designated by the same reference signs and are not explained several times over.

DETAILED DESCRIPTION

Figure 1:
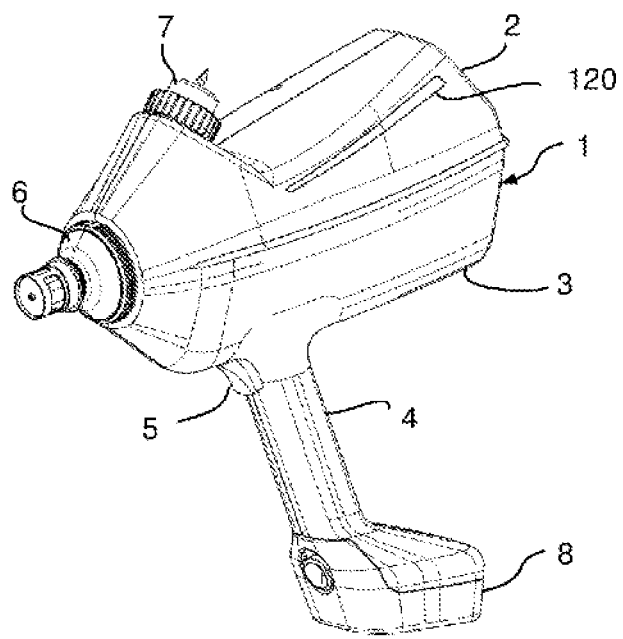
FIG. 1 shows a perspective view of an exemplary embodiment of the administering device 1.
Figure 2:
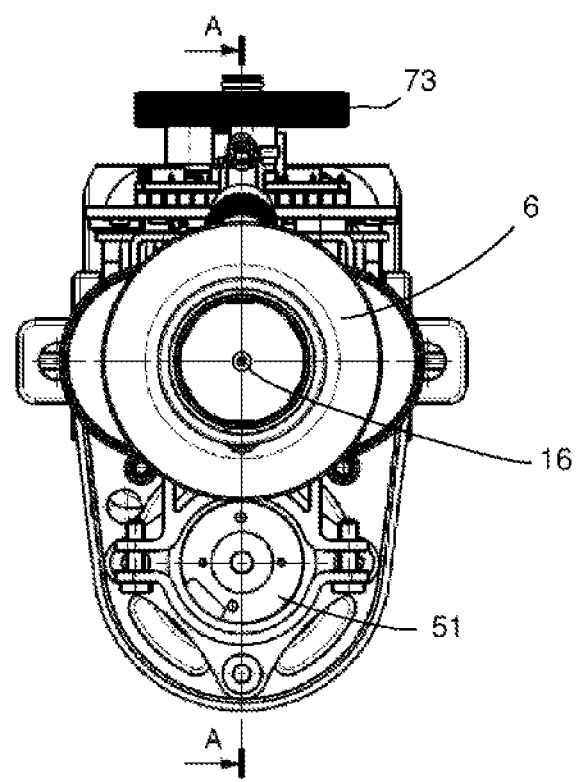
FIG. 2 shows a front view of the cylinder/piston arrangement 10 of the administering device 1.

In the exemplary embodiment shown in FIG. 1, the device 1 for administering a fluid (e.g. a liquid) comprises a housing 2 with a main portion 3 and a handle portion 4. The handle portion 4 is designed such that a user can hold the device 1 by grasping the handle portion. Furthermore, the handle portion 4 has a trigger 5 for actuating the device. A dispensing region 6 is formed at the front end of the main portion 3. Furthermore, at the top region of the main portion 3, the device 1 has an attachment 7 to which, for example, a hose or a container can be connected. The fluid that is to be administered can be delivered via the hose. Similarly, the fluid that is to be administered can be held in the container.

At its end facing away from the main portion 3, the handle portion 4 transitions into a base 8 in which, for example, a power supply (for example a storage battery) for the device 1 can be contained.

In the exemplary embodiment described here, the device 1, which can also be designated as an administering device 1, is designed for the needle-free administration of the fluid to an animal. The administration preferably involves an intramuscular injection of the fluid which, for example, can be a pharmaceutical product, a vaccine or the like.

The administering device 1 has a cylinder/piston arrangement 10 (FIGS. 3 and 4) described in more detail below and is of the self-filling type, such that a movement of the piston toward the dispensing region 6 causes a discharge of the fluid, and an opposite movement of the piston causes the cylinder to fill with the fluid for the next discharge procedure.

FIGS. 2 to 5 show the whole cylinder/piston arrangement 10 without the housing 2. The cylinder/piston arrangement 10 comprises a front part 11 and, connected to the latter, a rear part 12. The front part 11 comprises a cylinder 13 for receiving the fluid, which cylinder 13 has an open dispensing end 14 in which a nonreturn valve 15 sits, the latter being fluidically connected to a nozzle 16. The nonreturn valve 15 can also be seen clearly in the illustration according to FIG. 34 and is designed so as to permit dispensing of the fluid from the cylinder 13 via the nonreturn valve 15 and the nozzle 16. Suctioning of air or liquid via the nozzle and via the nonreturn valve 15 is not possible. The nonreturn valve 15 closes in this direction.

Also formed at the front part 11 is the attachment 7, in which a further nonreturn valve 20 (FIG. 3) sits, the latter permitting a fluidic connection of the attachment 7 to the cylinder 13 and blocking a fluidic connection in the opposite direction. The attachment 7 has a channel 21 which opens into the cylinder 13 via a plurality of radial bores 22.

The further nonreturn valve 20 can therefore be designated as an inlet valve and the nonreturn valve 15 can be designated as an outlet valve.

Figure 3:
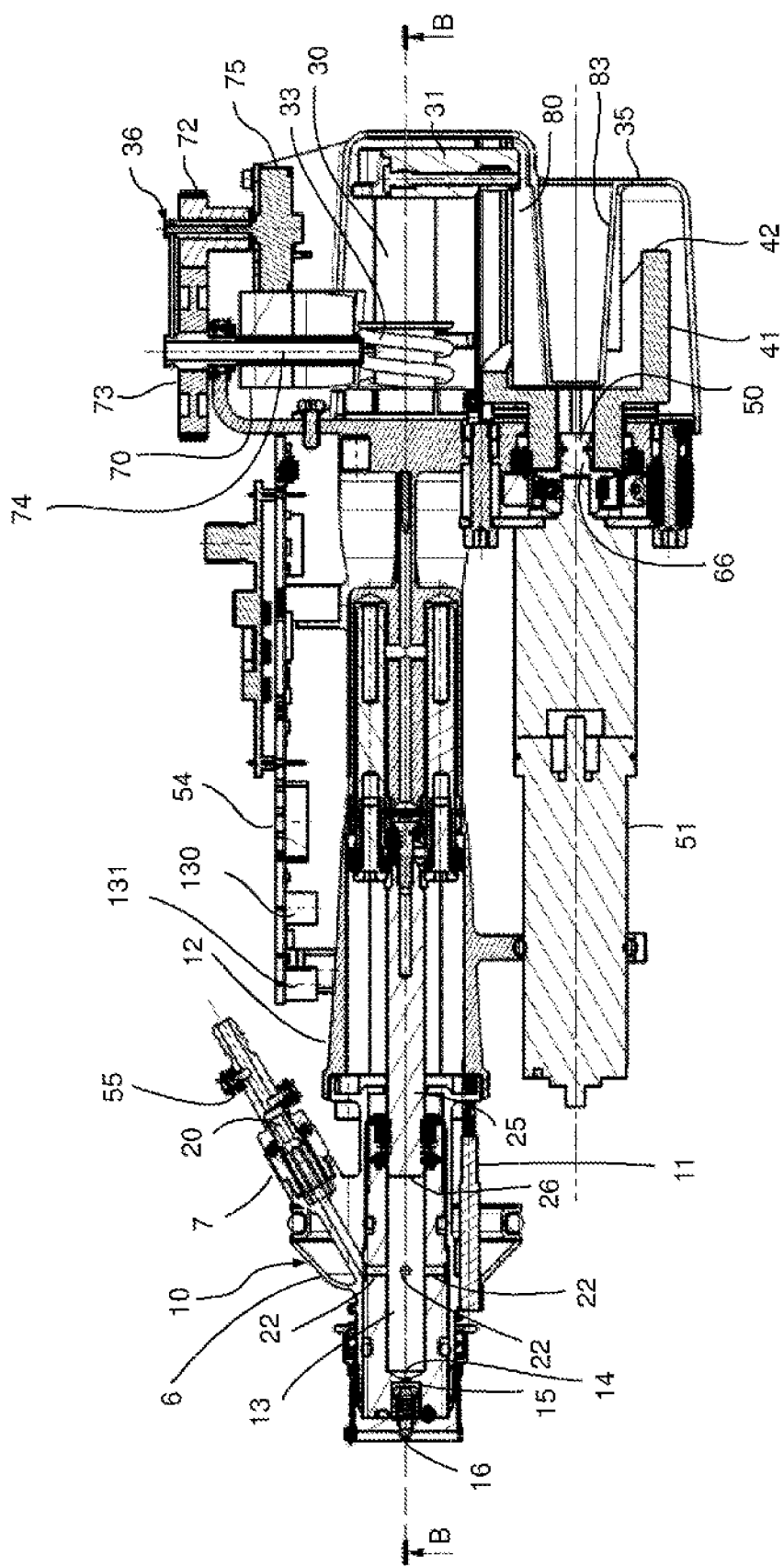
FIG. 3 shows a sectional view of the cylinder/piston arrangement 10 along the section line A-A in FIG. 2.
Figure 4:
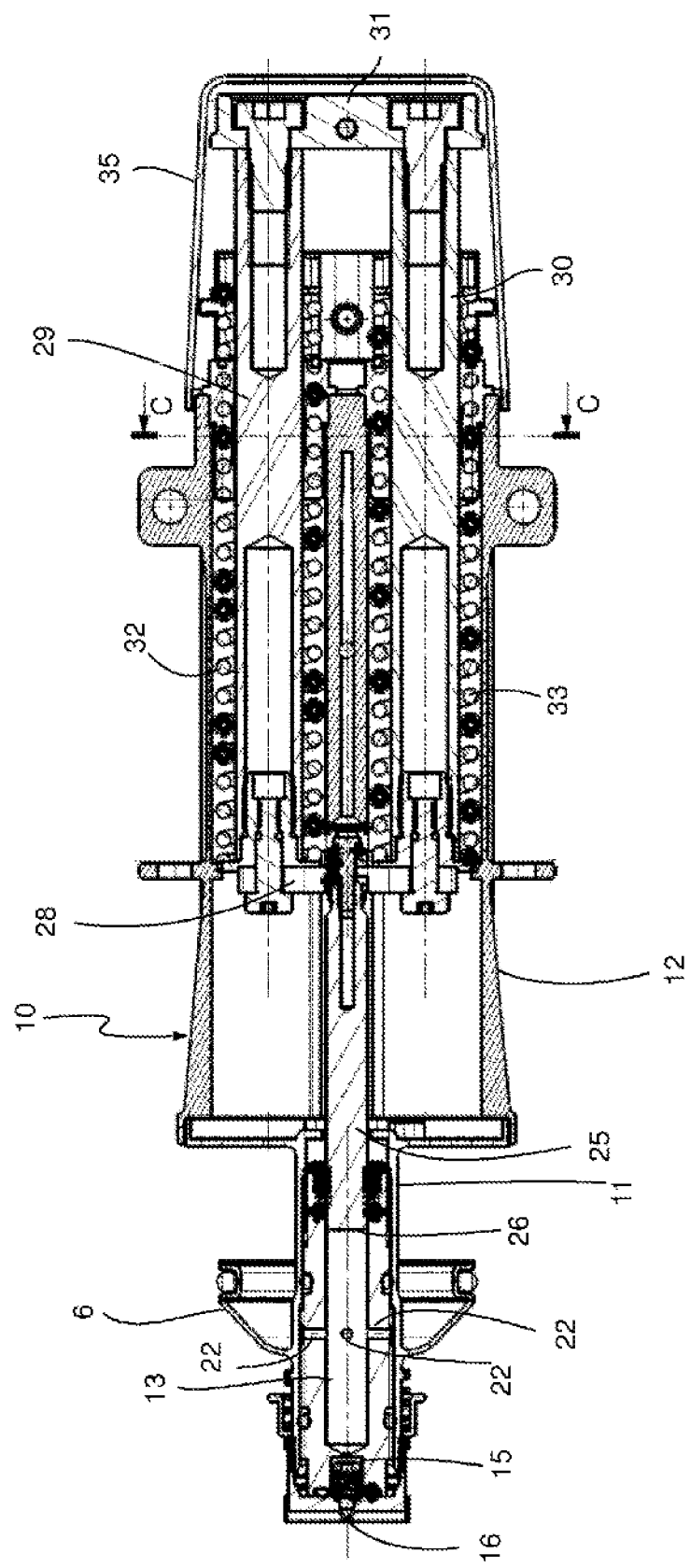
FIG. 4 shows a sectional view of the cylinder/piston arrangement 10 along the section line B-B in FIG. 3.
Figure 5:
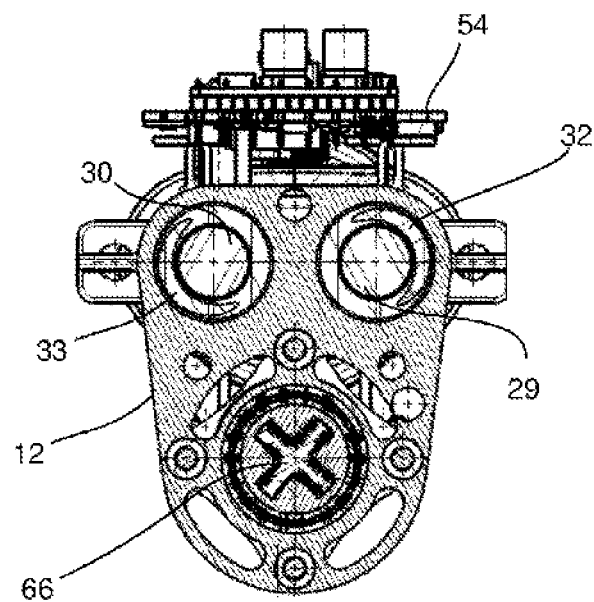
FIG. 5 shows a sectional view of the cylinder/piston arrangement 10 along the section line C-C in FIG. 4.

A piston rod 25 with a piston 26 formed at its end pointing toward the open dispensing end 14 is guided in the cylinder 13, wherein the piston 26 is in its rear end position in the sectional views in FIGS. 3 and 4. In this position, the cylinder 13 is filled with the fluid that is to be dispensed.

Figure 37:
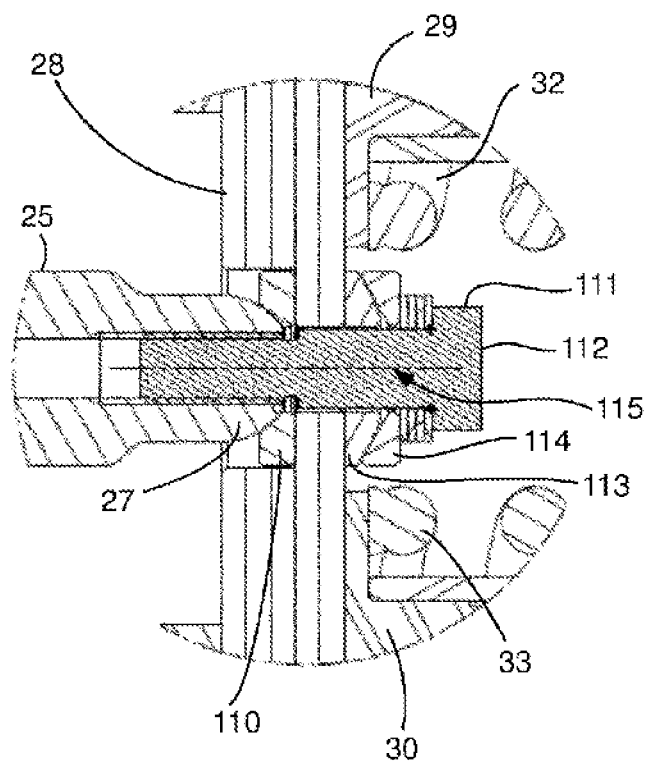
FIG. 37 shows an enlarged illustration of the detail A from FIG. 36.

The rear end 27 (shown clearly in FIG. 37) of the piston rod 25 pointing away from the open dispensing end 14 is connected by a plate 28 to a first guide rod 29 and a second guide rod 30, which extend parallel to each other and parallel to the piston rod 25 and are guided in the rear part 12 (FIG. 4). Those ends of the guide rods 29 and 30 facing away from the plate 28 are connected to a driver 31.

Moreover, a compression spring 32, 33 (e.g. a helical spring) is arranged for each guide rod 29 and 30, the front ends of the compression springs 32, 33 each bearing on the plate 28, and their rear ends each bearing on an abutment 34 of the rear part 12. In the position of the piston 26 shown in FIGS. 3 and 4, the springs 32, 33 are tensioned.

Figure 6:
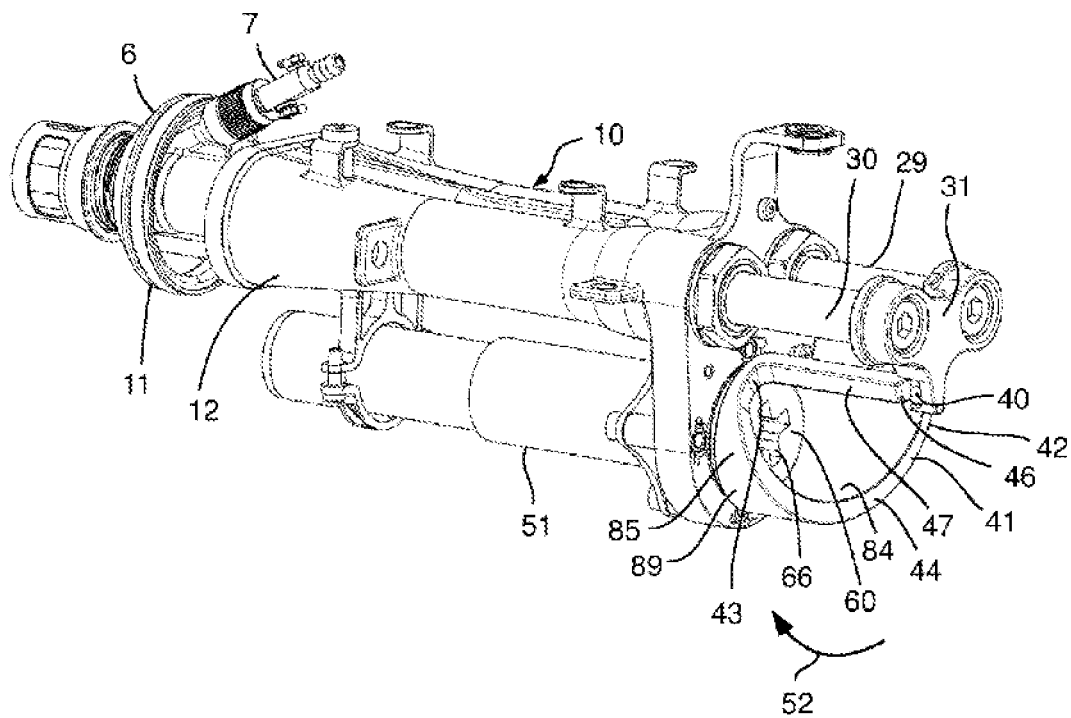
FIG. 6 shows an isometric view of the cylinder/piston arrangement 10, wherein the device is tensioned and the piston is in its rear end position.

Provided at the rear end of the rear part 12 is a cover 35 and a dose setting means 36, which are not shown in the isometric view of the cylinder/piston arrangement 10 according to FIG. 6 in order that the driver 31 can be clearly distinguished. The driver 31 has a rotatably mounted roller 40, wherein the rotation axis of the roller 40 extends substantially perpendicular to the longitudinal axis of the piston rod 25.

Figure 7:
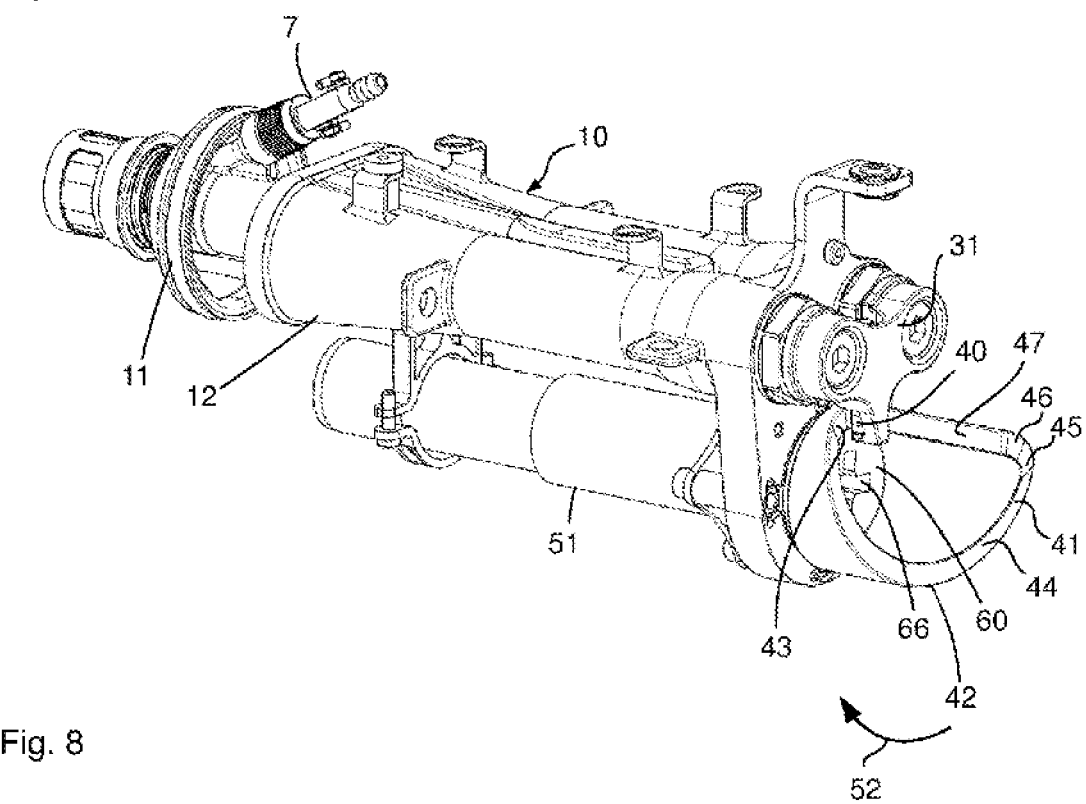
FIG. 7 shows an isometric view of the cylinder/piston arrangement 10, wherein the piston is in its front end position.
Figure 8:
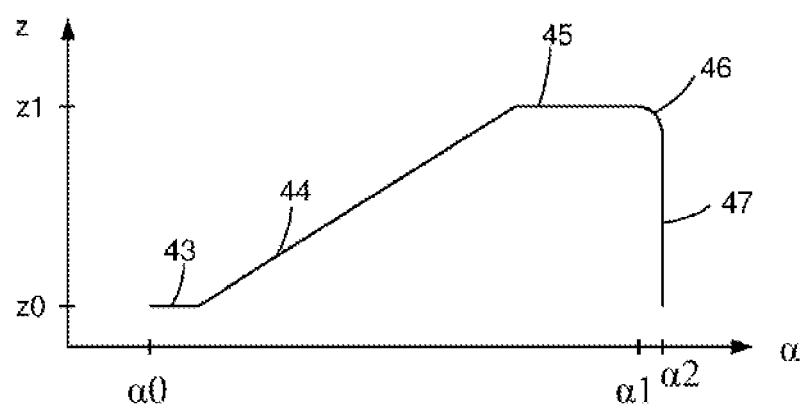
FIG. 8 shows a diagram for illustrating the profile of the ramp track 41, wherein the rotation angle α is plotted along the x axis, and the stroke along the longitudinal axis of the piston rod 25 is plotted along the y axis.
Figure 9:
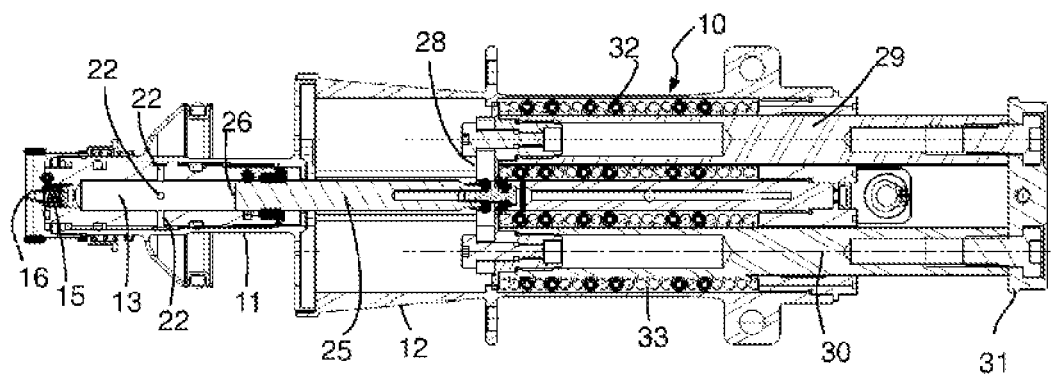
FIG. 9 shows a sectional view of the piston/cylinder arrangement 10 in the tensioned state according to FIG. 6.
Figure 10:
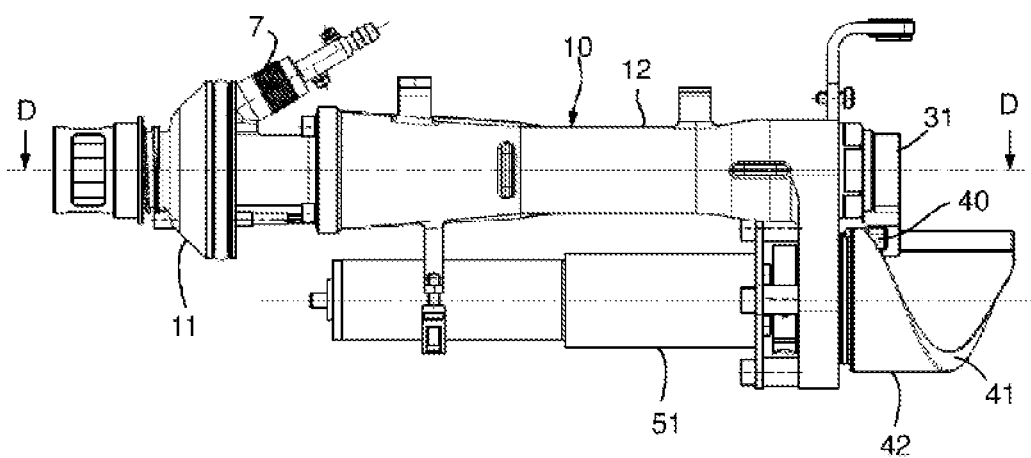
FIG. 10 shows a front view of the piston/cylinder arrangement 10, in which the piston is in its front end position.

The roller 40 runs on a ramp track 41 of a ramp 42 that rotates under the roller 40, wherein the ramp track 41 has a single winding, as can be seen in particular in FIGS. 6 to 8.

Figure 11:
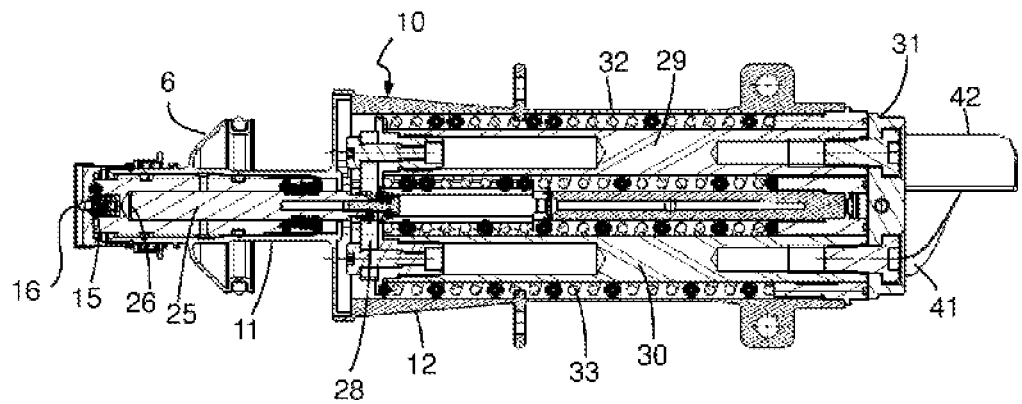
FIG. 11 shows a sectional view of the piston/cylinder arrangement 10 along the section line D-D in FIG. 10.

In FIG. 8, the rotation angle α is plotted with respect to the pitch difference z parallel to the longitudinal direction of the piston rod 25, wherein it is assumed that, at a rotation angle of α0=0°, the smallest pitch height z0 is present and the piston 26 is thus in a front end position, in which its distance from the open dispensing end 14 is minimal. This position of the piston 26 is shown for example in the sectional view according to FIG. 11.

The ramp track 41 has a lower plateau 43, which is adjoined by a region of inclination 44, the latter extending as far as the upper plateau 45. The upper plateau 45 is adjoined by a transfer region 46, which merges into a transition flank 47 (rotation angle α1), which in turn leads to the first plateau 43. The rotation angle range from α0 to α2 thus equals 360°.

The transition flank 47 is distinguished by the fact that it runs virtually vertically, since it extends from the height z1 to the height z0 at a rotation angle (here α2). The transfer region 46 is thus the rotation angle range at which the height z1 decreases continuously starting from the upper plateau 45, until the rotation angle α2 (=transition flank 47) is reached. Thus, the rotation angle range of α1 to α2 covers the transfer region 46.

The ramp 42 is connected by a coupling 50 to a motor 51 (FIG. 3) which rotates the ramp 42 in a first rotation direction 52 (FIGS. 6 and 7). If, starting from the position shown in FIG. 6 in which the cylinder/piston arrangement 10 is tensioned, the motor 51 now rotates the ramp 42 further in the first rotation direction 52 (since a user has actuated the trigger 5), the roller 40 runs over the transfer region 46 and then descends along the transition flank 47 in the direction of the lower plateau 43, since the tensioned compression springs 32 and 33 accelerate the plate 28 in the direction of the open dispensing end 14, as a result of which the piston rod 25 connected to the plate 28 is likewise moved toward the front dispensing end 14, and the fluid contained in the cylinder 13 is thereby discharged, via the nonreturn valve 15 and the nozzle 16, for intramuscular injection into an animal. The administering device 1 is designed such that the fluid safely penetrates the skin and is administered into the muscle lying below the latter. The piston 26 is then in its front end position, as is shown for example in the sectional view in FIG. 11. The administering device 1 is preferably configured such that, in the front end position of the piston 26, the driver 31 bears on the rear end of the rear part 12, as a result of which the rear end of the rear part 12 forms an abutment for the driver 31. In this position, there is still a desired minimal distance between the roller 40 and the ramp track 41, such that the lower plateau 43 of the ramp track 41 is not reached by the roller 40. It is thus possible to prevent the situation where the roller 40, at the end of the discharging procedure, strikes the ramp track 41, which could cause damage to the roller 40.

After the discharging procedure, the ramp 42 is rotated again in the first rotation direction 52 by means of the motor 51, such that, as soon as the roller 40 makes contact with the ramp track 41 in the region of inclination 44, further rotation has the effect that the driver 31 is moved along the longitudinal direction of the piston rod 25 away from the open dispensing end 14, as a result of which the compression springs 32, 33 are tensioned again and reach their maximum tensioning when the roller 40 reaches the upper plateau 45. On account of the mechanical connection of the driver 31 to the guide rods 29 and 30, to the plate 28 and to the piston rod 25, this movement of the driver 31 has the effect that the piston rod 25 and thus the piston 26 are also moved in a direction away from the open dispensing end in the cylinder 13, and a negative pressure is thus built up. As soon as the built-up negative pressure is so great that the inlet valve 20 opens, the fluid is sucked through the inlet valve 20 and the radial bores 22 into the cylinder 13, such that the cylinder 13 is filled with the fluid.

When the roller 40 (which can also be designated as a cam or roll) has reached the upper plateau 45, the motor 51 stops, such that the cylinder/piston arrangement 10 is tensioned and therefore the administering device 1 is ready for the next administering procedure, which can be carried out by actuating the trigger 5.

The plate 28, the springs 32, 33 and guide rods 29, 30, the driver 31 with the roller 40, and the ramp 42 form, together with motor 51 and coupling 50, a tensioning device S for tensioning the cylinder/piston arrangement 10.

The administering device 1 moreover comprises a control unit 54 for controlling the motor 51 and all the other electrical components of the device 1. FIG. 3 shows a printed circuit board with the control unit 54.

Figure 12A:
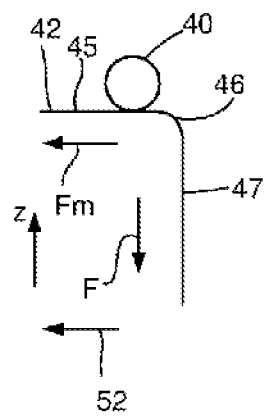
FIGS. 12A-12C show illustrations for explaining the forces when the roller 40 runs over the transfer region 46 toward the transition flank 47.
Figure 12B:
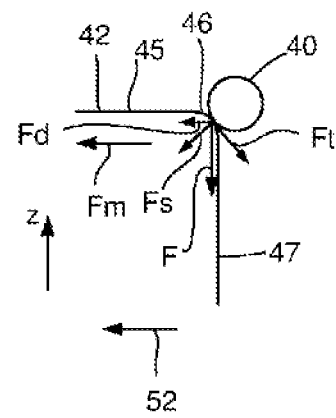
Figure 12C:
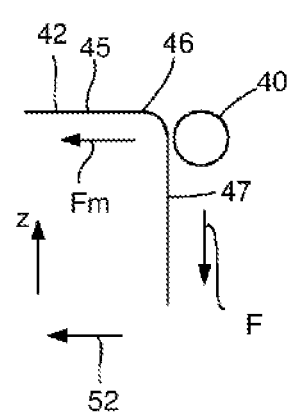

As has already been described, in order to administer the fluid, starting from the rotational position of the ramp 42 shown in FIG. 6, the ramp is rotated further in the first rotation direction 52, such that the roller 40 runs from the upper plateau 45 over the transfer region 46 and is then accelerated along the transition flank 47 toward the lower plateau 53. However, as it runs over the transfer region 46, there is the difficulty (FIGS. 12A-12C) that the spring force F of the tensioned springs 32, 33, in addition to a tangential component Ft, has a component Fs which is perpendicular to the latter and which comprises a component Fd which points in the same direction as the force of the motor Fm for rotating the ramp 42. As a result, the roller 40 running over the transfer region 46 accelerates the rotation of the ramp 42 (in addition to the rotation caused by the motor 51). This can disadvantageously lead to the motor 51 acting as a generator for this additional acceleration and generating a voltage peak which may damage the control electronics of the control unit 54. Furthermore, the motor 51 thereby acts as a brake, and therefore an undesirable braking effect occurs during the rotation of the ramp 42, the braking effect changing the pressure profile during the administering procedure in an undesirable manner.

The coupling 50 is therefore designed in such a manner that it transmits the torque provided by the motor 51 in order to rotate the ramp track 41 in the first rotation direction 52 and at the same time has a freewheel counter to the first rotation direction 52, the freewheel being configured in such a manner that it covers at least the rotation angle range (from α1 to α2) which corresponds to the transfer region 46 (here, e.g., 7°).

Figure 13:
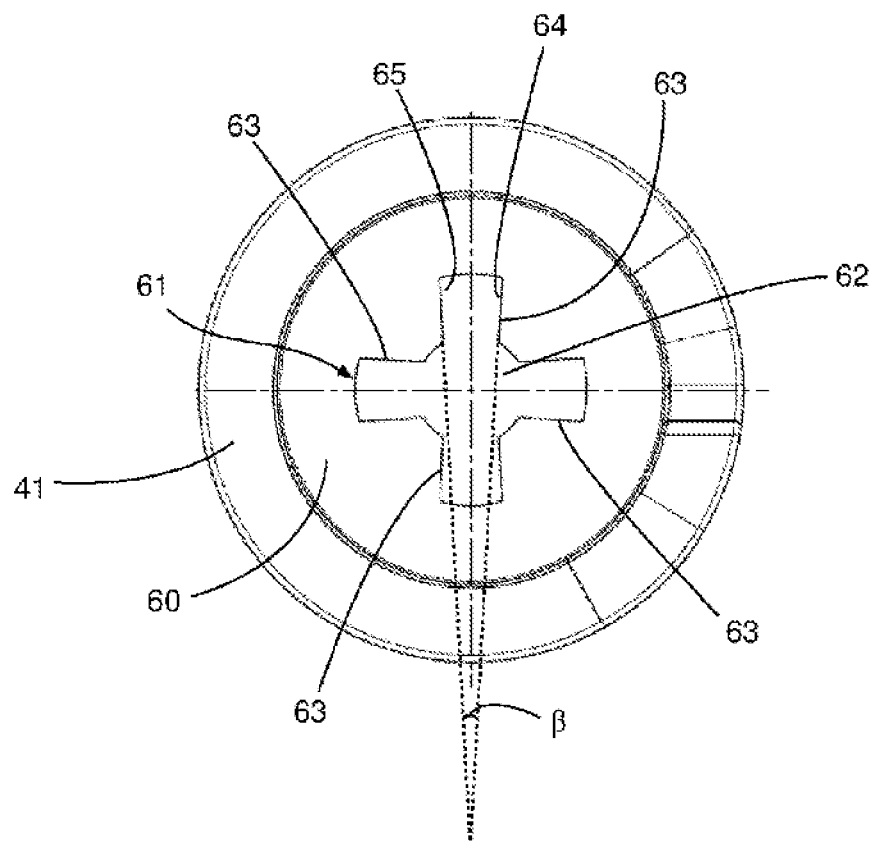
FIG. 13 shows a front view of the base 60 of the ramp 42.
Figure 14:
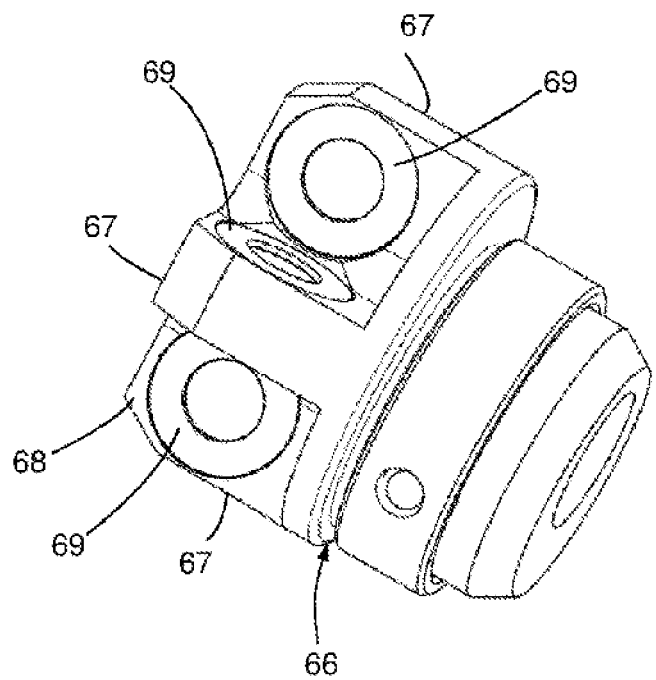
FIG. 14 shows an isometric view of the coupling part 66 connected to the motor 51 for conjoint rotation.
Figure 15:
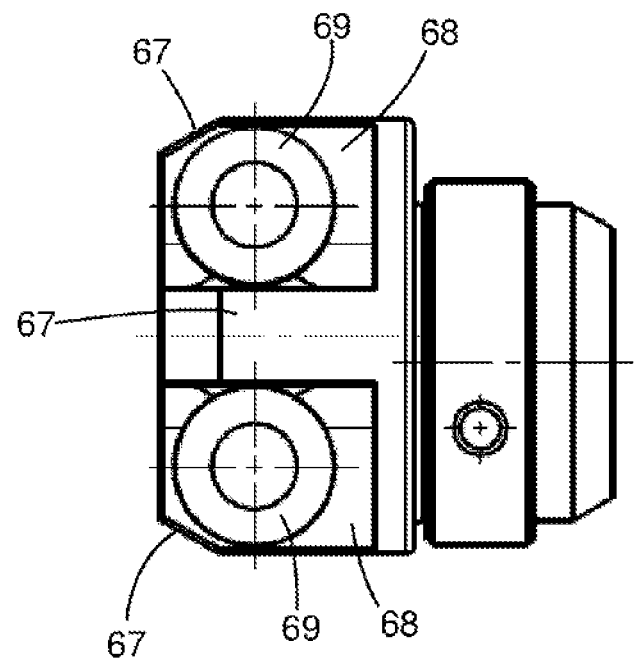
FIG. 15 shows a side view of the coupling part 66.
Figure 16:
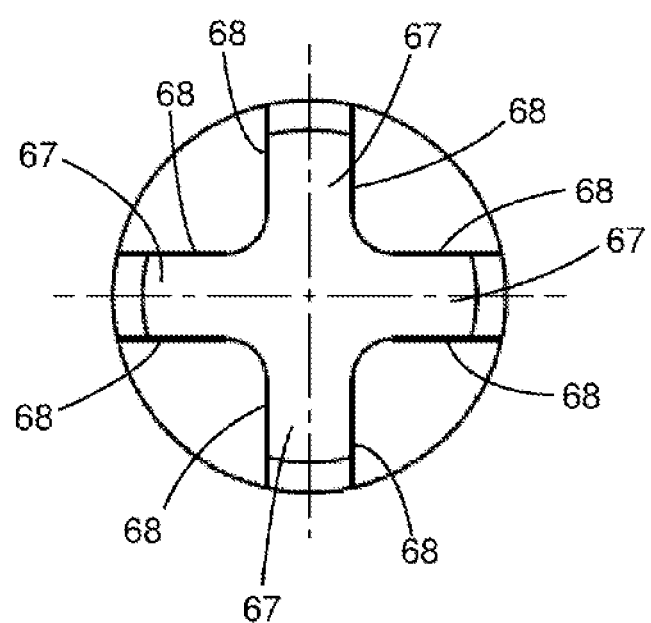
FIG. 16 shows a front view of the coupling part 66.

In order to form the coupling 50, a star-shaped recess 61 is formed in a base 60 of the ramp 42 (FIG. 13). The star-shaped recess 61 comprises a central portion 62 and four arms 63 which extend therefrom and are spaced apart from one another in each case by 90° in the circumferential direction. As FIG. 13 shows schematically for one of the arms 63, the side surfaces 64, 65 of the arms 63 are inclined with respect to one another such that they enclose an angle β which corresponds at least to the rotation angle of the transfer region 46 and therefore here to 7°.

Figure 17:
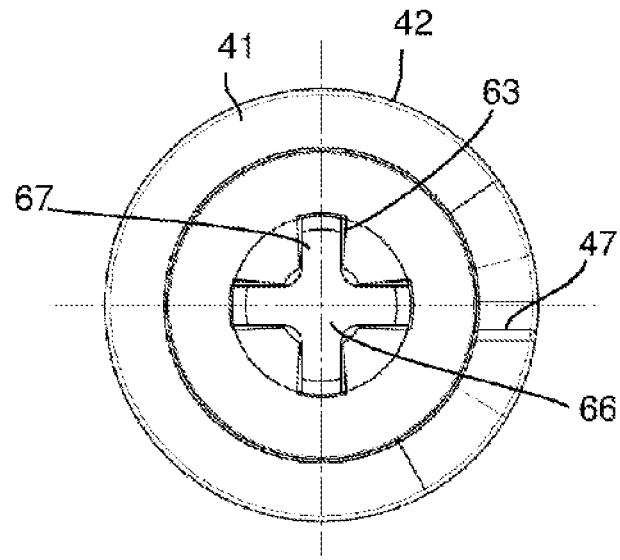
FIG. 17 shows a front view of the coupling part 66 inserted into the recess 61 in the base 60.

Furthermore, the coupling 50 comprises a coupling part 66, which is connected to the motor and which has four walls 67 which are arranged in a star-shaped manner and are spaced apart from one another in each case by 90° in the circumferential direction. A spring 69 (here disk spring) is arranged on each side surface 68 of each wall. The springs 69 serve for supporting the movement and for damping. The walls 67 of the star-shaped contour of the coupling part 66 are inserted into the star-shaped recess 61 of the base 60 of the ramp 42, as shown in the front view according to FIG. 17. Owing to the springs 69, each wall 67 is centered in the corresponding arm 63 of the star-shaped recess 61 if torque is not transmitted via the coupling 50.

Figure 18:
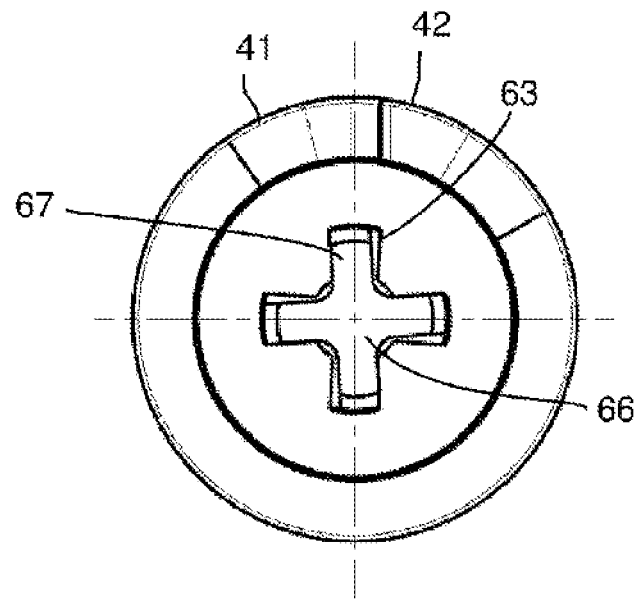
FIGS. 18 and 19 show illustrations according to FIG. 17 for explaining the freewheel provided by the coupling 50.

If the roller 40 is rotated in the first rotation direction 52 by means of the motor 51, the front side surfaces 68, which are seen in the first rotation direction 52, bear on the corresponding side surface 64 of each arm 63, as shown in FIG. 18.

Figure 19:
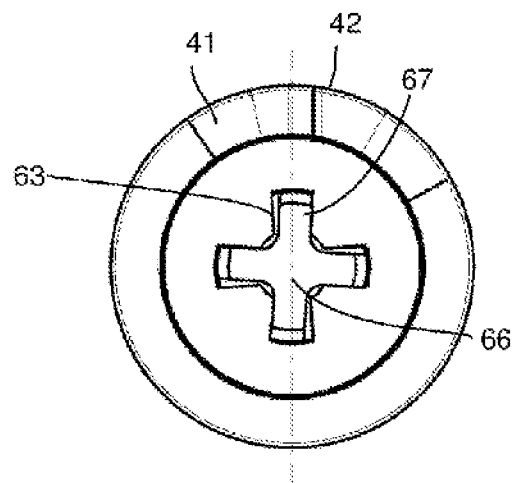

If, starting from the upper plateau 45, the roller 40 runs over the transfer region 46, the spring force described (here the component Fd) additionally accelerates the ramp 42 in the first rotation direction 52, such that, owing to the freewheel which is provided, the ramp 42 can rotate more rapidly in the first rotation direction 52 than the coupling part 66 which is connected to the motor 51. This freewheel ends as soon as the rear side surface 68 of the respective wall 67, which rear side surface is seen in the first rotation direction 52, bears on the side surface 65 of the corresponding arm 63 of the star-shaped recess 61, as shown in FIG. 19. Since the freewheel is configured in such a manner that it covers at least the entire transfer region 46, the roller 40 is moved beyond the entire transfer region 46 as soon as the contact according to FIG. 19 is present. The roller 40 can therefore move freely along the transition flank 47, and the undesirable acceleration of the rotational movement of the motor 51 as the roller runs over the transfer region 46 is reliably avoided.

Figure 20:
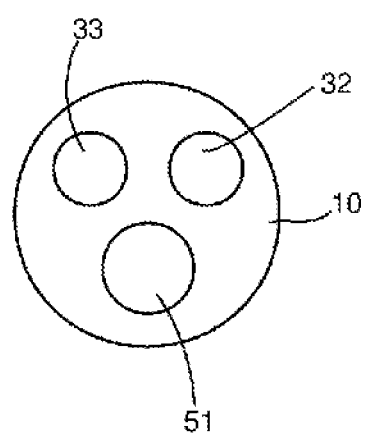
FIG. 20 shows a schematic front view of the spatial arrangement of the springs 32 and 33 and of the motor 51.
Figure 21:
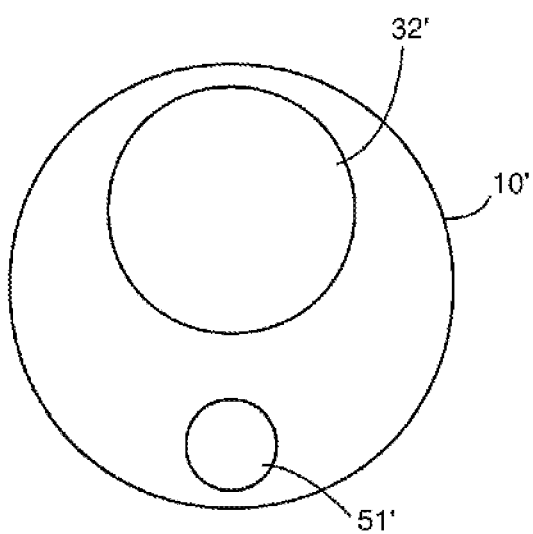
FIG. 21 shows a comparison view of the arrangement of a spring and of the motor of a conventional administering device.

FIG. 20 shows a schematic front view which shows the spatial arrangement of the springs 32 and 33 and of the motor 51. The two springs 32 and 33 are connected in parallel by the plate 28 such that their spring rates (spring constants) add up. Therefore, when the piston 26 is in its rear end position, the required force (spring force) can be provided, the force being necessary to so greatly accelerate the piston 26 that the fluid being dispensed can be administered intramuscularly to an animal. At the same time, the required construction space for the cylinder/piston arrangement 10 can be kept small and compact. As a comparison with the illustration in FIG. 21 shows, in which only one spring 32' is provided instead of the two springs 32 and 33, this would lead to a greater construction space for the corresponding cylinder/piston arrangement 10' since said individual spring 33' would have to have a larger diameter in order to provide the same spring force.

Figure 22:
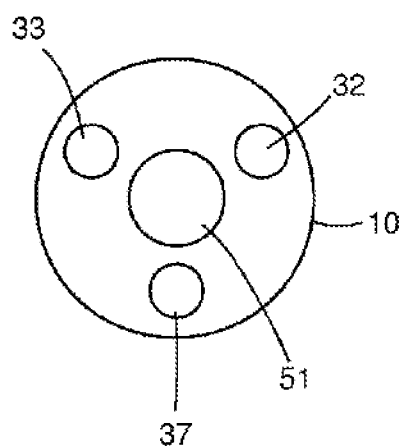
FIGS. 22 and 23 show further views of further exemplary embodiments for the spatial arrangement of spring and motor in the administering device 1.
Figure 23:
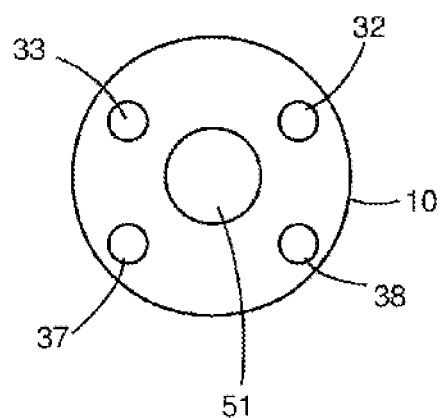

Of course, it is also possible to connect more than two springs 32 and 33 in parallel. As can be seen in the schematic illustrations of FIGS. 22 and 23, it is possible, for example, to provide three or four springs 32, 33, 37 and optionally 38 in order to realize a compact constructional form. The more than two springs (here three or four springs) can preferably be arranged symmetrically with respect to the motor 51, as shown in FIGS. 22 and 23.

Figure 24:
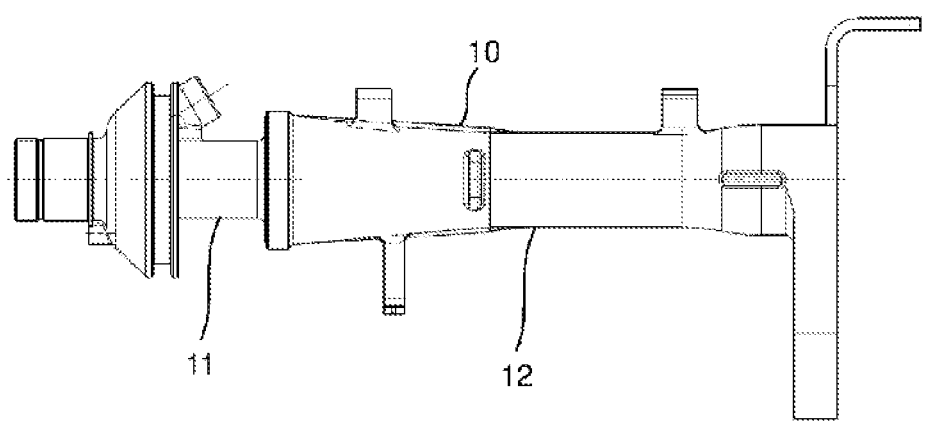
FIG. 24 shows a view of the front part 11 and rear part 12 in the connected state.
Figure 25:
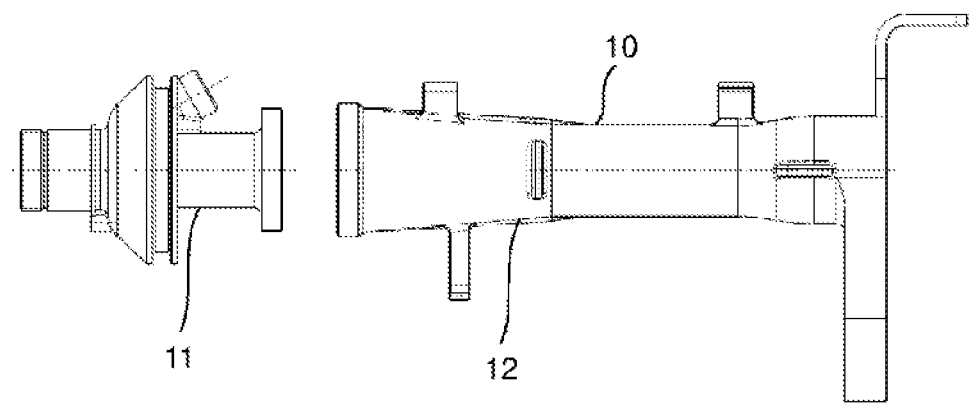
FIG. 25 shows a view of the front part 11 and of the rear part 12 in the non-connected state.

As has already been explained, the front part 11 and the rear part 12 are two separate parts which are connected to each other, as can also be clearly seen in the illustrations in FIGS. 24 and 25.

The front part 11 and the rear part 12 are preferably formed from different materials. Since the front portion of the front part 11 protrudes from the housing 2 (FIG. 1), a material is selected for it that has, for example, a greater strength than the material for the rear part and/or that has a better media stability than the material of the rear part 12.

The material of the front part 11 can thus comprise titanium, steel or plastic (e.g. PEEK).

For the material of the rear part 12, in particular a material is selected which has as little weight as possible. Aluminum, magnesium, titanium or plastic are preferred here.

Figure 26:
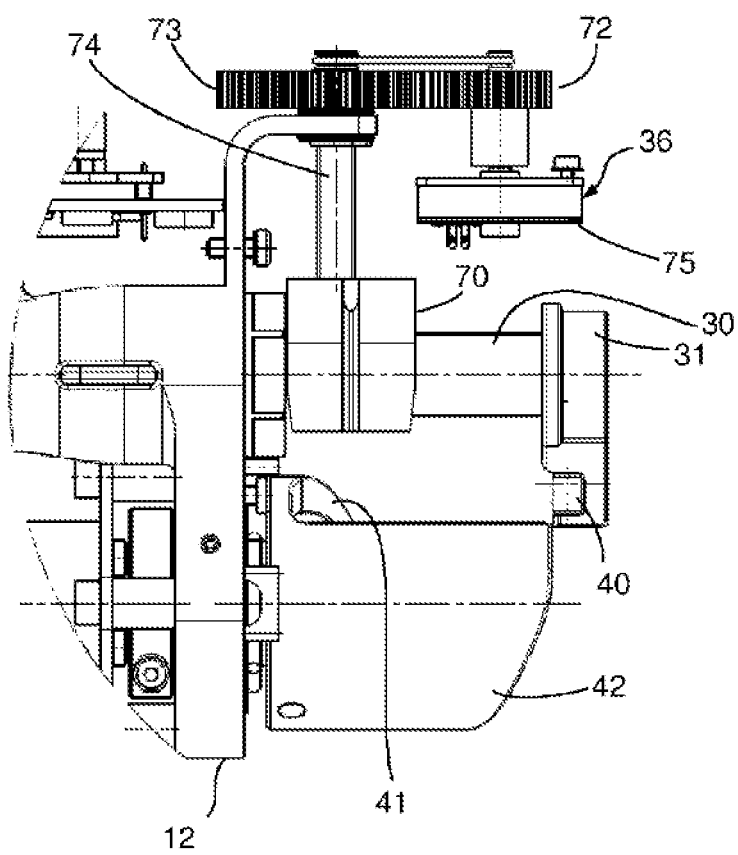
FIG. 26 shows an enlarged detailed view of the dose setting means 36.
Figure 27A:
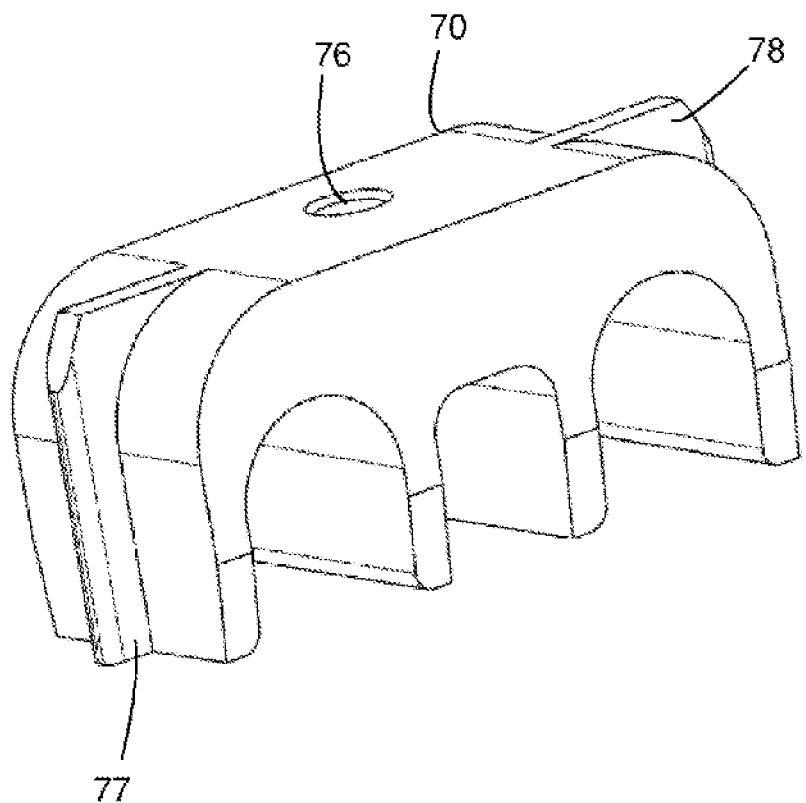
FIG. 27A shows a perspective view of the spacer 70.

As can be seen in particular in the enlarged detailed sectional view in FIG. 26 and FIG. 27A, the dose setting means 36 comprises a spacer 70 into which a threaded rod 71 is screwed that is coupled by a first and second gearwheel 72, 73 to a shaft 74 of a second motor 75. The threaded rod 71 is screwed into a threaded bore 76 in the spacer 70 (FIG. 3). Furthermore, the spacer 70 comprises two laterally protruding guide webs 77, 78 (FIG. 27A). The guide webs 77, 78 are guided in guide grooves 79 of the covering 35. The guide grooves 79 can best be seen in FIG. 28. Furthermore, the cover 35 comprises an opening 80 through which the spacer 70 can be moved.

In the illustration according to FIG. 3, the spacer 70 is in its neutral position in which it does not affect the return movement of the roller 40, and therefore of the driver 31, from the upper plateau 45 over the transfer region 46 along the transition flank 47 toward the lower plateau 43. In FIG. 26, the spacer 70, by contrast, has been moved into its active position in which it is positioned between the driver 31 and the rear end of the rear part 12 in such a manner that it forms an abutment for the driver 31. The movement of the spacer from the position shown in FIG. 3 to the position shown in FIG. 26 is produced by rotation of the shaft 74, wherein, for example, a right-hand rotation of the shaft 74 brings about a movement from the position shown in FIG. 3 to the position shown in FIG. 6, and a left-hand rotation of the shaft 74 brings about an opposite movement. Of course, the dose setting means 36 can also be configured in such a manner that the reverse rotation directions bring about the same movements. It is essential here that, by means of the second motor 75, the two gearwheels 72 and 73 and therefore the shaft 74 can be rotated in order to convert said rotational movement into a translational movement of the spacer 70 perpendicularly to the longitudinal direction of the piston rod 25. The spacer 70 can therefore be moved to and fro between its active position and its neutral position.

If the spacer 70 is now in the active position shown in FIG. 26, the movement of the driver 31 in the longitudinal direction of the piston rod 25, after the roller 40 has run over the transfer region 46, is shortened since said movement now ends when the driver 31 bears on the spacer 70. The extent of the spacer 70 along the longitudinal direction of the piston rod 25 therefore corresponds to the shortening of the piston stroke during the administering of the fluid located in the cylinder 13. A smaller amount of fluid can therefore be discharged, as a result of which two different doses can be administered with the administering device 1 (here e.g. 2 ml and 1 ml). If the dose is intended to be changed, all that needs to be done, if the roller 40 is on the upper plateau 45, is for the spacer 70 to be brought into its active position shown in FIG. 26.

The spacer 70 is designed in such a manner that, when the driver 31 bears on it, the roller 40 has no contact with the spacer 70. This prevents the roller 40 from being damaged by the spacer 70 when the driver 31 is stopped.

Figure 27B:
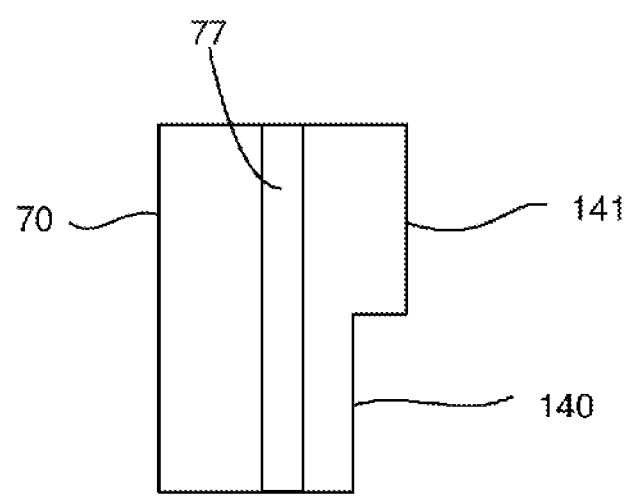
FIG. 27B shows a schematic illustration of a further exemplary embodiment of a spacer 70.

With the described spacer according to FIG. 27A, it is therefore possible to set a single smaller dose, as has been described. FIG. 27B shows a modification of the spacer 70, with which it is possible to set two different smaller doses since the spacer 70 has a first abutment region 140 and a second abutment region 141 which differ by the extent of the spacer 70 along the first direction (from the left to the right in FIG. 27B). Since this extent corresponds to the reduction in the stroke of the piston 26 during the administering procedure, two different reductions of the dose are possible. If the spacer 70 is retracted to such an extent between the driver 31 and the rear end of the rear part 12 that the driver 31 is stopped by the portion 140 during the administering procedure, a first reduction of the piston stroke is present. If, by contrast, the spacer 70 is retracted to such an extent that the driver 31 bears on the region 141 during the administering procedure, a second reduction of the piston stroke is then present which is greater than the reduction by means of the portion 140. This stepped design of the spacer 70 therefore makes it possible to set two different reductions of the dose.

Figure 28:
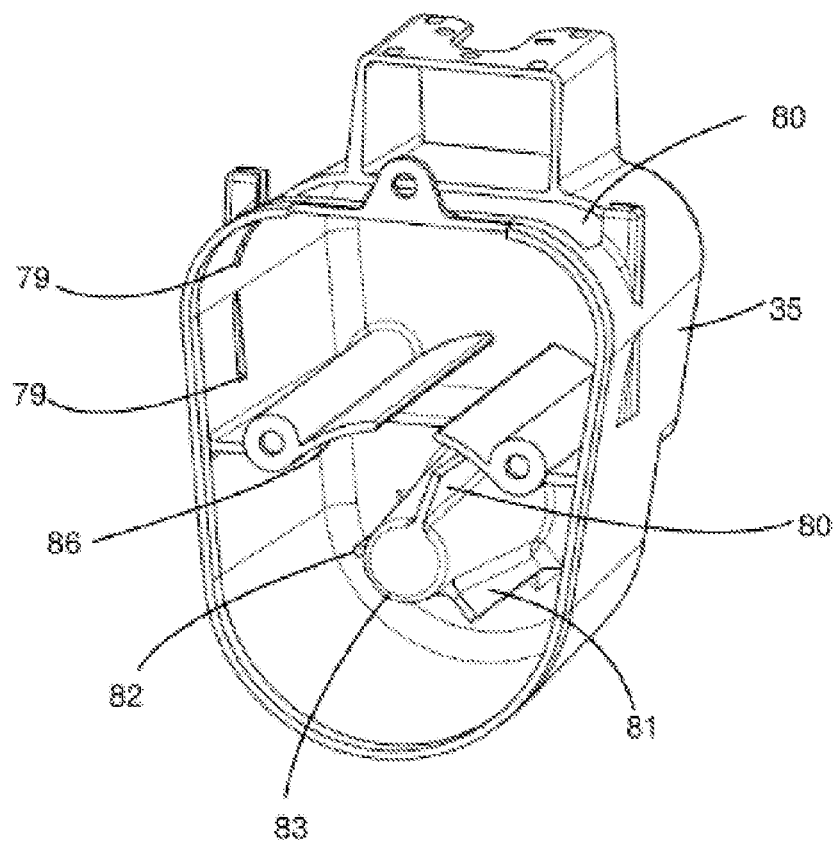
FIG. 28 shows a perspective illustration of the cover 35.
Figure 29:
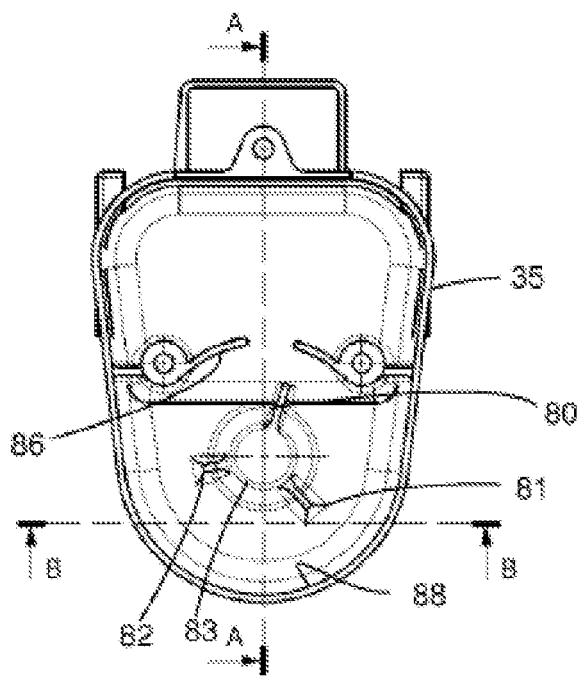
FIG. 29 shows a front view of the cover 35.
Figure 30:
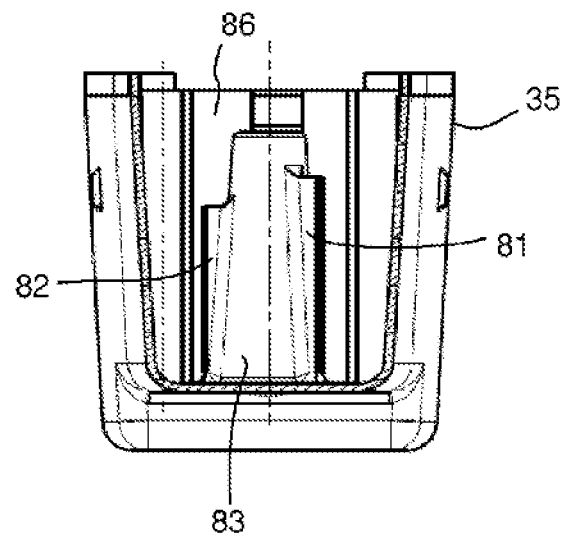
FIG. 30 shows a sectional view along the section line B-B in FIG. 29.
Figure 31:
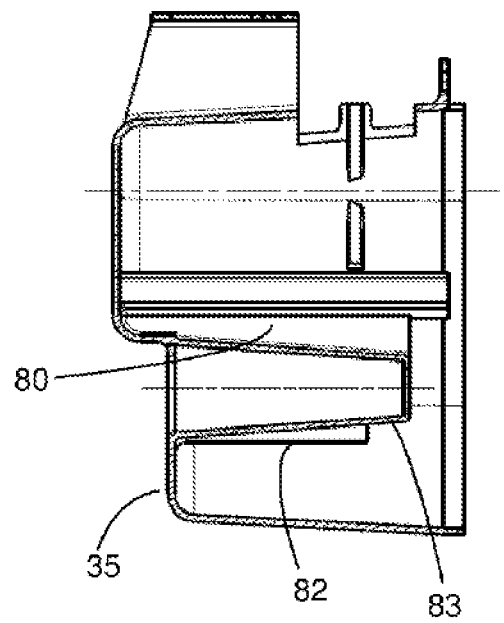
FIG. 31 shows a sectional view along the section line A-A in FIG. 29.
Figure 32:
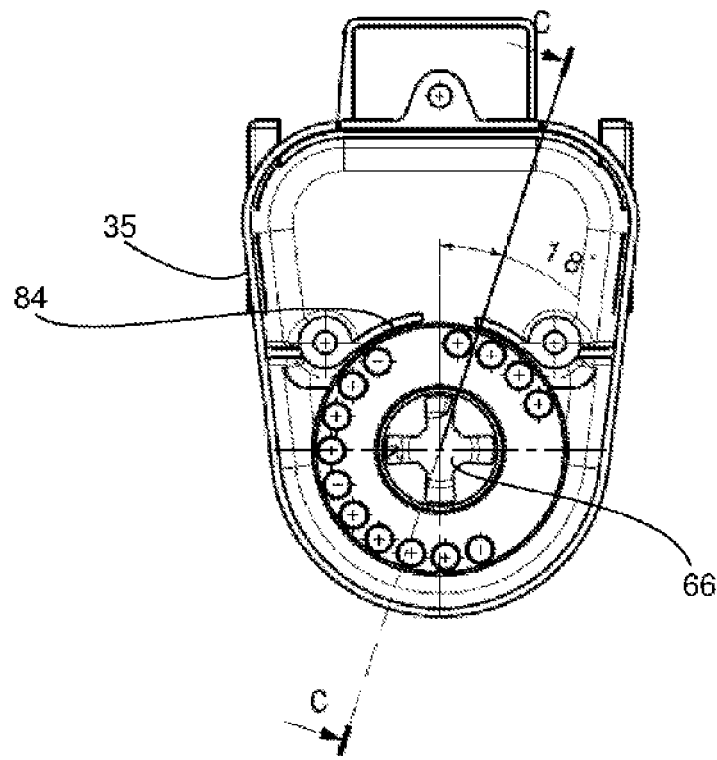
FIG. 32 shows a front view of the cover 31.
Figure 33:
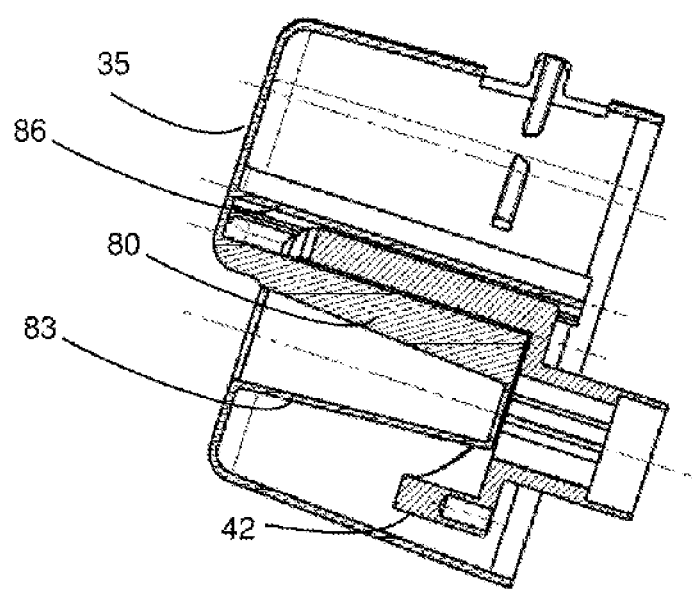
FIG. 33 shows a sectional view of the cover 35 along the section line C-C in FIG. 32.

As can clearly be seen for example in FIG. 28, the cover 35 comprises a first, second and third scraper 80, 81, 82 which, in the assembled state according to FIG. 3, extend from a rear end of the cover 35 in the direction towards the dispensing end of the administering device 1. As can be seen for example in FIG. 28, the scrapers 80-82 are formed on a frustoconical central portion 83 and is spaced apart from one another in the circumferential direction. The frustoconical central portion 83 tapers in the direction toward the dispensing end, as is apparent in FIG. 3.

In the assembled state, the frustoconical central part 83 extends as far as the base 60 of the ramp 41. In the same way, the first scraper 80 extends as far as the base 60. The first scraper 80 extends in the radial direction as far as the inner side 84 of the wall 85, on the front face of which the ramp track 42 is formed (FIG. 6).

The second scraper 81 is shorter than the first scraper 80 both in the axial direction and in the radial direction. In the same way, the third scraper 82 is shorter than the second scraper 81 in the radial direction and axial direction.

Furthermore, the cover 35 comprises an intermediate wall 86 in which a slot extending in the axial direction is formed, in which slot the roller 40 together with its holding portion of the driver 31 can move in the axial direction. Otherwise, the intermediate wall 86 together with the lower cover part 88 surrounds the outer side 89 of the wall 85 in the assembled state. A lubricant (for example grease) is provided in said remaining space between the cover 35 and the wall 85, the lubricant being used such that the roller 40 is rotated as smoothly as possible and is guided with as little friction as possible on the ramp track 41. By means of the scrapers 80 to 82, the grease which does not remain on the ramp track 41 is moved again, because of the relative movement between ramp track 41 and the scrapers 80-82, in the direction of the ramp track and roller 40, and therefore permanent lubrication can be ensured. The lubricant which accumulates at the bottom in the cover 35 is therefore conveyed again to the ramp track 41 and to the roller 40, and therefore the desired permanent lubrication is ensured.

Figure 34:
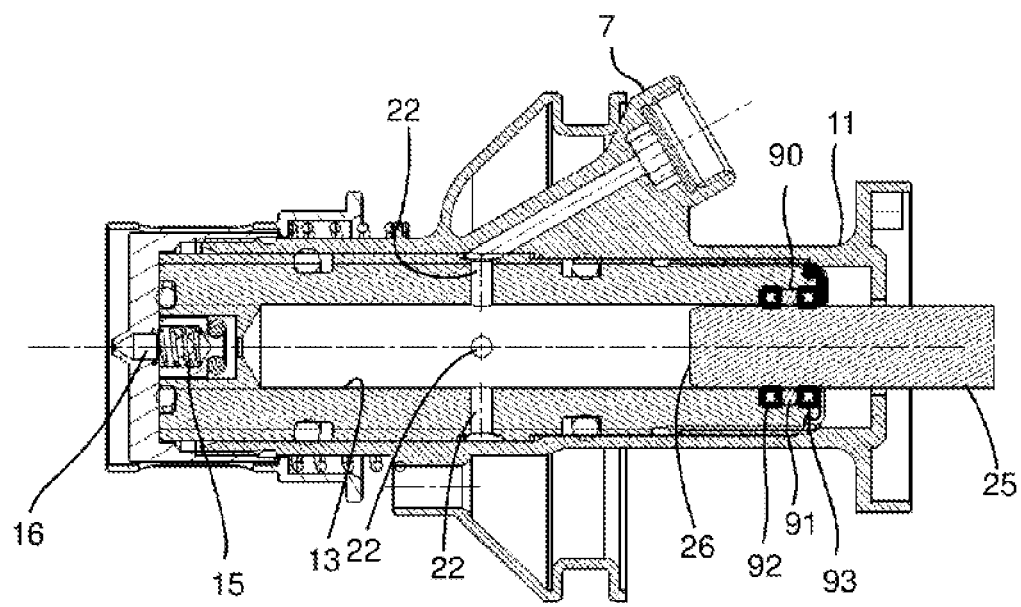
FIG. 34 shows an enlarged sectional illustration of the front part 11 together with piston 26 and part of the piston rod 25.

FIG. 34 shows an enlarged sectional view of the front part 11 together with piston 26 and part of the piston rod 25. The cylinder 13 has, in its rear region (facing away from the open dispersing end 14), an annular groove 90 in which an O ring 91 or a sealing ring 91 (e.g. an elastomer seal) is inserted for sealing purposes. Furthermore, a first and a second support ring (92, 93) are arranged in the grove 90 in such a manner that the sealing ring 91 is positioned between the two support rings 92 and 93. The groove 90 and the support rings 92 and 93 are dimensioned in such a manner that the gap between the support rings 92 and 93 and the piston rod 25 is smaller than between the inner side of the cylinder 13 and the piston rod 25. The support rings, which can be produced, for example, from PTFE or other plastics, reliably avoid part of the sealing ring 91 being extruded into the gap between the piston rod 25 and the inner side of the cylinder 13 because of the pressure or negative pressure built up during movement of the piston rod 95, which would destroy the sealing ring 91.

The second support ring 93 prevents the described gap extrusion during a movement of the piston rod 25 towards the open dispensing end 14 and therefore during the administering of the fluid. The first support ring 92 prevents the undesired gap extrusion during the opposite movement and therefore during filling of the cylinder 13 with the fluid.

Figure 35:
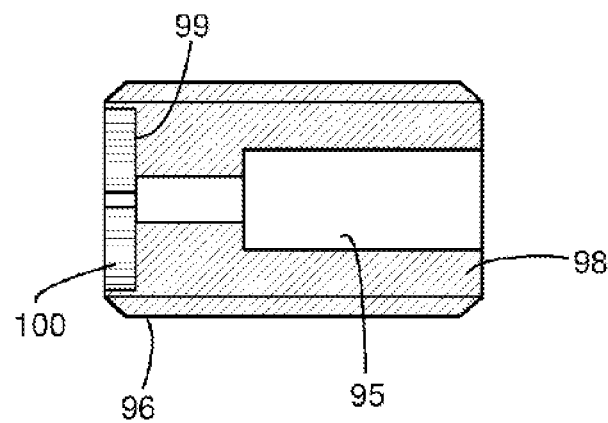
FIG. 35 shows a schematic sectional illustration of an insert 96 for the nozzle 16.

As can be seen in FIG. 34, the nozzle 16 has a tapering through bore 95 through which the fluid is dispensed during the administration. The required through bore 95 can also be formed in an insert 96, as is shown in FIG. 35, which is then to be screwed into the remaining main nozzle body 97. The insert 96 comprises a basic body 98 with an external thread which comprises a receiving region 99 at the distal end. A sapphire element 100 in which the final portion of the through bore 95 is formed is inserted into the receiving region 99. As can be gathered from the illustration in FIG. 35, the diameter of the final portion of the through bore 95 is the smallest or is smaller than the diameter of those portions of the through bore 95 which are formed in the basic body 98. The effect is therefore advantageously achieved that the required very small diameter of the through bore 95 can be reliably produced at its distal end since the portion of the through bore 95 in the sapphire element 100 can be manufactured more precisely than a bore in the basic body 98 which is produced from metal. The diameter of the final portion of the through bore 95 in the sapphire element 100 can be, for example, in the range of 0.30 to 0.38 mm, with the intention being that the manufacturing tolerance is not greater than 0.02 mm.

Since the unit consisting of piston rod 26, plate 28 and guide rods 29, 30 is relatively long and high forces act during the administering of the fluid, it has to be ensured that the piston rod 26 can move freely in the cylinder 13 and, for example, does not tilt. For this purpose, the piston rod 26 should be oriented, for example, as far as possible parallel to the guide rods 29, 30 and this should also continue to remain over the long term during the use of the administering device 1.

Figure 36:
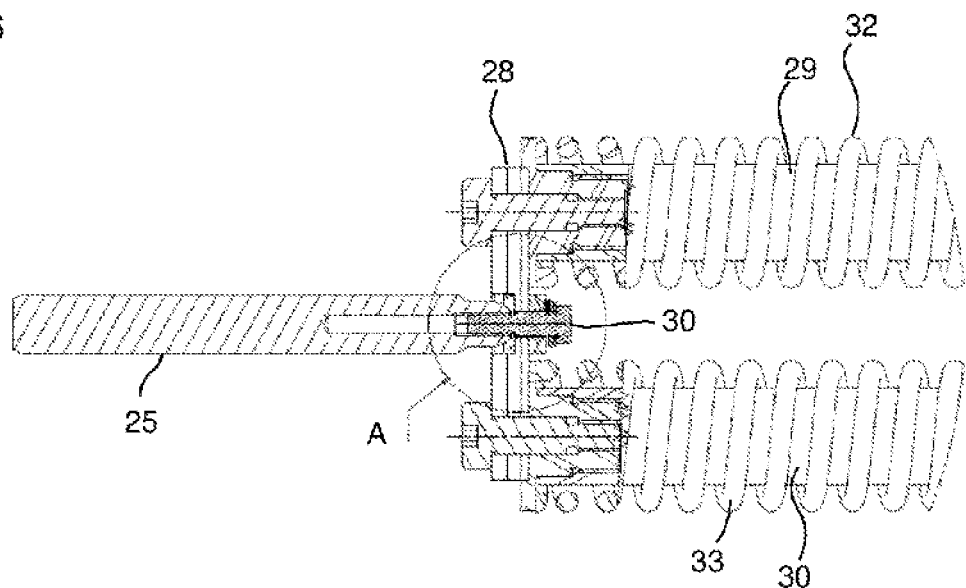
FIG. 36 shows a schematic sectional illustration of piston rod 25, plate 28 and guide rods 29 and 30 and springs 32 and 33.

The piston rod 25 is therefore not connected absolutely rigidly to the plate 28. The connection is configured in such a manner that tipping or locating of the piston rod 26 in relation to the plate 28 is possible. The piston rod 25 is therefore connected to the plate 28 via a swivel joint. As can be gathered from the illustrations in FIGS. 36 and 39, a first washer 110 is provided between the rear end 27 of the piston rod 25 and the plate 28. Furthermore, a fixing screw 111 which runs through a corresponding bore in the plate 28 is screwed into the rear end 27. A second and a third washer 113, 114 are arranged between a head 112 of the fixing screw 111. In order to provide the desired rotatability, the rear end 27 is rounded (here, for example, spherically), and that side of the first washer 110 which faces the rear end 27 is correspondingly concave such that this side forms a bed for the rear end 27. As can be gathered from the illustration in FIG. 37, the first washer 110 sits in a depression in the plate 28 such that the first washer 110 cannot move transversely with respect to the longitudinal direction of the piston rod 25. That side of the first washer 110 which faces away from the rear end 27 is flat since the corresponding bottom of the recess in the plate 28 is also flat. The first washer can therefore also be designated with being plano-concave.

The second and third washers 113 and 114 are designed in such a manner that the mutually facing sides are in turn curved. In this case, that side of the second washer 113 which faces the third washer 114 has a convex curvature. That side of the third washer 114 which faces the second washer 113 is correspondingly concavely curved. The other sides of the second and third washers 113, 114 are flat. The head 112 of the fixing screw 111 presses the third washer 114 onto the second washer 113 which is thereby pressed against that side of the plate 28 which faces away from the rear end 27. The second washer 113 is therefore plano-convex and the third washer 114 is therefore plano-concave.

By means of the selected measurements and curvatures, the rotation point 115 for the rotation of the piston rod 25 relative to the plate 28 is spaced apart from the plate 28 and on the side of the screw head 112.

Since the described connection permits rotation of the piston rod 25 relative to the plate 28, it can be ensured that the piston rod 25 can always be moved in the cylinder 13 without becoming wedged.

The motor 51 can be designed as an electric motor and in particular as a brushless electric motor. The durability of the administering device 1 is therefore improved since, in the case of an electric motor with brushes, the difficulty may occur that, due to the vibrations which occur during the administering of the fluid, the brushes may break.

In order to identify whether fluid is in the cylinder 13 in the position of the piston 26 shown in FIG. 3, a sensor 55 is provided which, in the exemplary embodiment described here, is provided upstream of the further nonreturn valve 20 (which can also be designated as inlet valve). The sensor 55 can, for example, distinguish air from liquid, and it can thereby be avoided that the administering device 1 carries out an administering procedure if there is no liquid in the cylinder 13. Damage to the administering device 1 can therefore be prevented since the latter is configured such that the liquid damps the movement of the piston rod 25 or of the piston 26 toward the open dispensing end during the administration. If there is no liquid in the cylinder 13, said damping function is omitted, as a result of which mechanical damage, for example, to the piston rod 25, to the connection of the piston rod 25 to the plate 28 or to the guide rods 29, 30 may occur. The sensor 55 can be designed as a voltage sensor, as a capacitive sensor or, for example, as a light barrier.

The housing 2 can have an illuminating region 120 (FIG. 1) which can light in different colors. The region 120 can be, for example, strip-shaped or else can have any other form. User information regarding the state of the administering device 1 can be shared using the different colors. For example, a first color (for example the color red) can be used to share with the user that the device 1 is not ready to be used. A second color can be used to share that it is basically ready for operation. A third color can be used to share that the cylinder/piston arrangement 10 is tensioned and, by actuation of the trigger 5, an administering procedure can be carried out. A fourth color (for example green) can be used to share with the user that the administering procedure was successful. Furthermore, a further color can be used to share with the user that there is an error state. Of course, the described information can be shared not only via different colors, but also via identical colors if the differences are depicted, for example, by flashing in different ways. Furthermore, it is possible to provide haptic or acoustic feedback for the user rather than said described visual feedback. Of course, the visual, haptic and acoustic feedback can also be combined.

Figure 38:
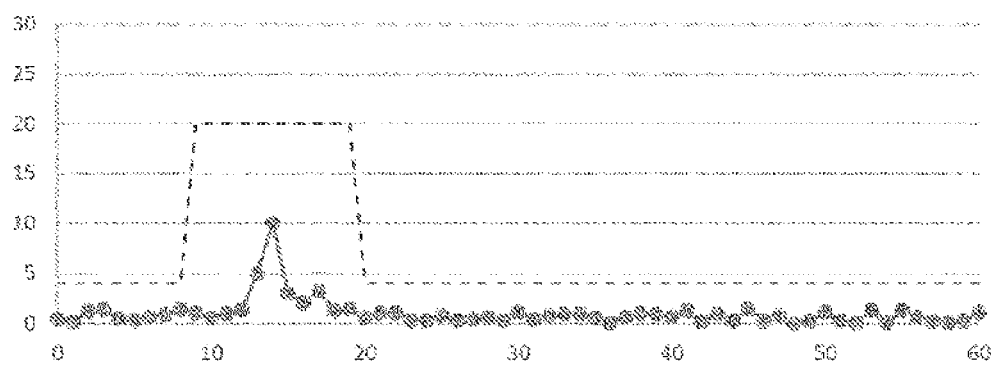
FIGS. 38 and 39 show diagrams with measurement values of acceleration values measured during the tensioning procedure and dispensing procedure.

Furthermore, the administering device 1 can have an acceleration sensor 130 which is shown by way of example only in FIG. 3. Since the measured acceleration values for a correct administering procedure differ from those of an incorrect administering procedure, it can be determined on the basis of the measured values whether an administering procedure was successful or not. In FIG. 38, the measured acceleration values for a successful administering procedure are plotted along the y axis in g (=gravitational acceleration) over time along the x axis (in ms). The measured acceleration values are depicted as points which are connected by a line. A test curve is shown by dashed lines. If the acceleration values lie below the values of the test curve, it is determined that the administering procedure was successful.

Figure 39:
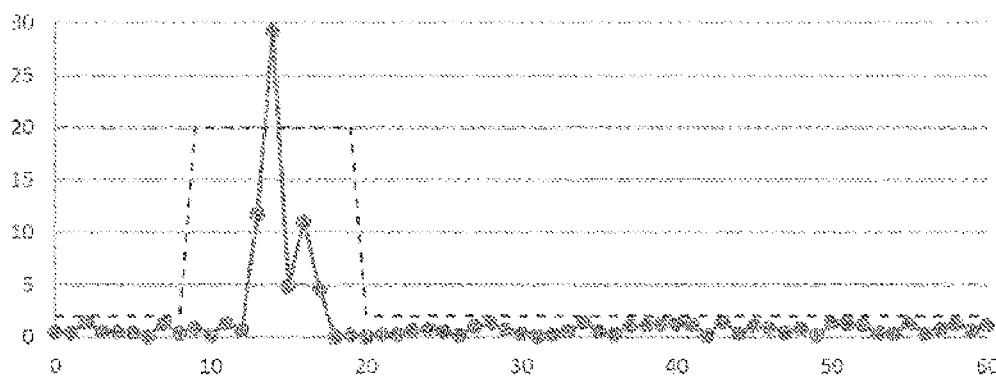

FIG. 39 shows an example of an administering procedure (which is also designed below as a shot) which was not successful. The acceleration values exceed the maximum value of the test curve, and therefore an unsuccessful shot should be assumed.

Furthermore, the current consumption of the motor 51 can be measured and evaluated to assess the quality of the shot.

Figure 40:
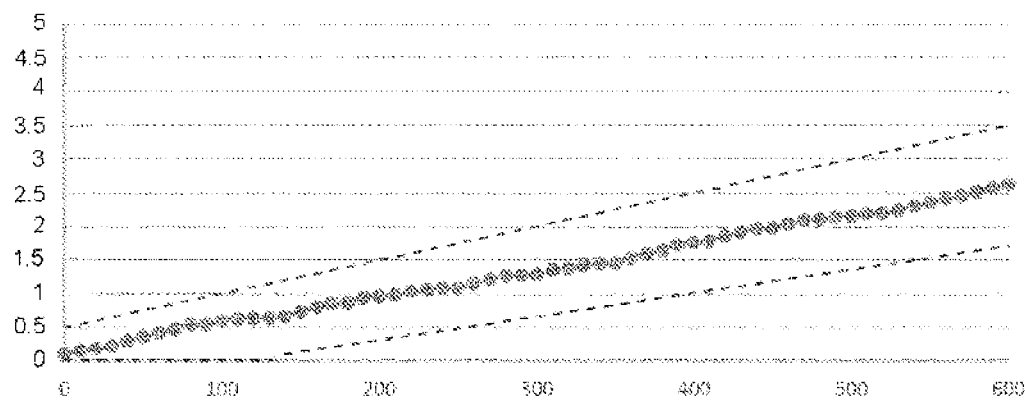
FIGS. 40 and 41 show diagrams with measurement values of the current consumption of the motor 51 measured during a tensioning procedure and dispensing procedure.

FIG. 40 shows the measured current consumption for the charging and shot procedure of the administering device 1, wherein the measured current values in A (=ampere) are shown as points which are connected by a line. The current value is plotted along the y axis (over time in ms along the x axis). A successful charging and shot procedure is present whenever the measured current values are smaller than the upper limit value curve and greater than the lower limit value curve (both curves are shown by dashed lines).

Figure 41:
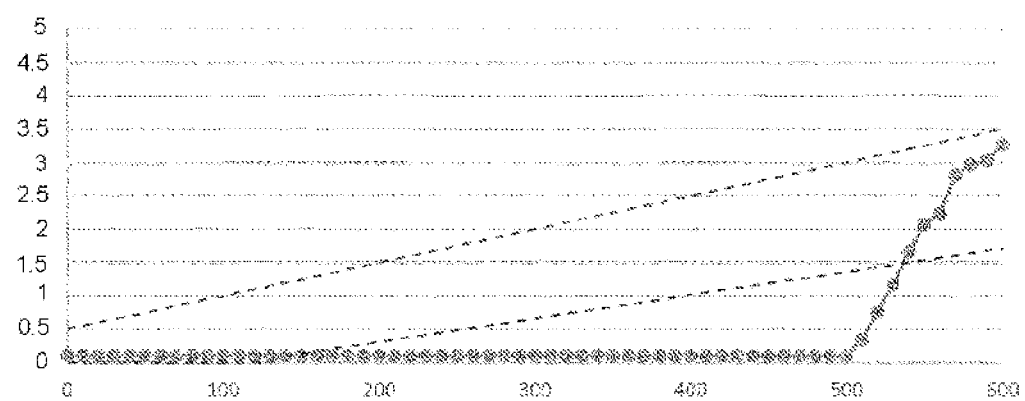

If a shot is unsuccessful, the measured current value lies outside the range delimited by the two limit value curves, as illustrated in FIG. 41. In this case, the administering procedure was not successful.

Instead of or in addition to the acceleration sensor 130, a sensor 131 can be provided for measuring sound or pitches (e.g. a microphone) which is illustrated schematically in FIG. 3. On the basis of the pitches during the dispensing procedure it can be determined, for example, whether the administering procedure was successful or not. If the temporal profile of the measured pitch is, for example, higher than a predefined upper limit or a temporal profile of the upper limit is, the administering procedure is assessed as being unsuccessful. The temporal profile of the measured pitch, e.g. a temporal profile of a lower limit, may also be fallen short of, which can lead to the conclusion that an administering procedure was erroneous. It is also possible, for example, to evaluate a measured frequency spectrum as a characteristic variable, which frequency spectrum has to carry out a desired temporal profile in order for the administering procedure to be evaluated as being successful. In the same way, the temporal profile of the intensity (or volume) can be used as a characteristic variable which in turn has to carry out a desired temporal profile.

Of course, use may also be made of a plurality of the described characteristic variables in order to carry out the evaluation of the administering procedure. For example, only the dispensing procedure, only the tensioning procedure or the tensioning procedure and the dispensing procedure together can be measured and evaluated here.

The control unit 54 can carry out the described measurement and evaluation of the characteristic variables in order to determine whether the administering procedure was successful or not. Depending on the determination, the control unit can generate, for example, visual, haptic and/or acoustic feedback in the manner described.

While the invention has been described in connection with what is presently considered to be the most practical and preferred embodiments, it will be apparent to those of ordinary skill in the art that the invention is not to be limited to the disclosed embodiments. It will be readily apparent to those of ordinary skill in the art that many modifications and equivalent arrangements can be made thereof without departing from the spirit and scope of the present disclosure, such scope to be accorded the broadest interpretation of the appended claims so as to encompass all equivalent structures and products. Moreover, features or aspects of various example embodiments may be mixed and matched (even if such combination is not explicitly described herein) without departing from the scope of the invention.

The invention claimed is:

1. A device for administering a fluid, comprising:
a cylinder, which has an open dispensing end;
a piston, which is displaceable in the cylinder between a front end position and a rear end position, and is connected to a piston rod which, along a first direction, protrudes from a rear end of the cylinder opposite the open dispensing end;
a nonreturn valve closing the open dispensing end;
a tensioning device connected to the piston rod; and
a control unit,
wherein the tensioning device moves the piston rod along the first direction in a tensioning procedure until the piston is in the rear end position, thereby filling the cylinder with the fluid to be administered and pretensioning the piston rod toward the open dispensing end, and
wherein the tensioning device, when the piston is in the rear end position, releases the piston rod in a dispensing procedure such that, owing to the pretension which is present, the piston is moved counter to the first direction toward the open dispensing end and, in the process, fluid in the cylinder is dispensed via the nonreturn valve for administration,
wherein the tensioning device includes a ramp which is rotatable via a motor, and a ramp track extending along a helical line,
wherein the ramp track ascends from a first plateau along a region of inclination to a second plateau, and descends from the second plateau to the first plateau via a transition flank,
wherein the ramp track has a transfer region connecting the second plateau and the transition flank,
wherein the tensioning device includes a roller which is in contact with the ramp track and which is mounted rotatably in a driver, the driver being connected to the piston rod, and therefore, upon rotation of the ramp along a first rotation direction, the ramp track runs below the thus rotating roller,
wherein, during the tensioning procedure, the ramp track is rotated along the first rotation direction such that the roller runs on the region of inclination as far as the second plateau, and the piston is thereby moved to its rear end position,
wherein, during the dispensing procedure, starting from a contact of the roller with the second plateau, the ramp track rotates along the first rotation direction until the roller runs over the transfer region and, on account of the tensioning, accelerates toward the first plateau and, as a result, the piston moves toward the open dispensing end, and
wherein the control unit measures a characteristic variable during a tensioning procedure and/or dispensing procedure, and determines therefrom, by comparing with at least one specified value, whether the tensioning procedure and/or dispensing procedure has taken place correctly.

2. The device of claim 1, wherein the current consumption of the motor during the tensioning procedure is the characteristic variable.

3. The device of claim 2, wherein a temporal desired profile of the current consumption with a lower limit and an upper limit is predefined as the at least one specified value, and wherein the control unit determines the tensioning procedure as being correct when the current consumption measured throughout the entire tensioning procedure is not smaller than the lower limit and not larger than the upper limit.

4. The device of claim 1, wherein an acceleration acting on the device for administration purposes during the dispensing operation is the characteristic variable.

5. The device of claim 4, wherein a temporal desired profile of the acceleration with an upper limit is predefined as the at least one specified value, and wherein the control unit determines the dispensing procedure as being correct when the acceleration measured throughout the entire dispensing operation is not greater than the upper limit.

6. The device of claim 1, wherein a frequency spectrum of a sound of the device during the dispensing procedure is the characteristic variable.

7. The device of claim 6,
wherein a first upper desired frequency and a first lower desired frequency, and/or a first upper desired amplitude and a first lower desired amplitude are predefined as the at least one specified value, and
wherein the control unit determines the dispensing procedure as being correct when a main frequency of a measured frequency spectrum lies between the first upper desired frequency and the first lower desired frequency and/or the amplitude of the main frequency of the measured frequency spectrum lies between the first upper desired amplitude and the first lower desired amplitude.

8. The device of claim 6,
wherein a second upper desired frequency and a second lower desired frequency and/or a second upper desired amplitude and a second lower desired amplitude are predefined as the at least one specified value, and
wherein the control unit determines the dispensing procedure as being correct when a first secondary frequency of a measured frequency spectrum lies between the second upper desired frequency and the second lower desired frequency and/or the amplitude of the first secondary frequency of the measured frequency spectrum lies between the second upper desired amplitude and the second lower desired amplitude.

9. The device of claim 1, wherein a duration of the tensioning procedure is the characteristic variable.

10. The device of claim 9, wherein a first desired duration is predefined as the at least one specified value, and wherein the control unit determines the tensioning procedure as being correct when the duration is greater than the first desired duration.

11. The device of claim 9, wherein a second desired duration is predefined as the at least one specified value, and wherein the control unit determines the tensioning procedure as being correct when the duration is smaller than the second desired duration.

12. The device of claim 1, wherein a rotation angle covered by the ramp track along the first rotation direction during the tensioning procedure is the characteristic variable.

13. The device of claim 12, wherein a desired rotation angle is predefined as the at least one specified value, and wherein the control unit determines the tensioning procedure as being correct when the rotation angle which is covered is greater than the desired rotation angle.

14. The device of claim 1, wherein the control unit carries out the measurement of the characteristic variable during the dispensing procedure and the tensioning procedure and, by comparing with the at least one specified value, determines whether both the tensioning procedure and the dispensing procedure have taken place correctly.

* * * * *